(12) United States Patent
Walker et al.

(10) Patent No.: US 7,821,404 B2
(45) Date of Patent: Oct. 26, 2010

(54) SYSTEMS AND METHODS FOR IMPROVED HEALTH CARE COMPLIANCE

(75) Inventors: Jay S. Walker, Ridgefield, CT (US); James A. Jorasch, 240 E. 39th St., Apartment 42B, New York, NY (US) 10016; Patrick W. Nee, Jr., Old Greenwich, CT (US); Carson C. K. Fincham, Ridgefield, CT (US); Evan Walker, Ridgefield, CT (US); David Bean, Ormand Beach, FL (US); Rajivan Maniam, Bridgewater, NJ (US)

(73) Assignee: James A. Jorasch, New York, NY (US)

( * ) Notice: Subject to any disclaimer, the term of this patent is extended or adjusted under 35 U.S.C. 154(b) by 1000 days.

(21) Appl. No.: 11/424,082

(22) Filed: Jun. 14, 2006

(65) Prior Publication Data
US 2006/0276931 A1      Dec. 7, 2006

Related U.S. Application Data

(63) Continuation of application No. 11/255,240, filed on Oct. 20, 2005, which is a continuation-in-part of application No. 10/835,422, filed on Apr. 29, 2004, now Pat. No. 7,553,234, which is a continuation-in-part of application No. 09/165,089, filed on Oct. 1, 1998, now Pat. No. 6,751,730.

(51) Int. Cl.
*G08B 23/00* (2006.01)
(52) U.S. Cl. ........................ 340/573.1; 340/321; 463/43
(58) Field of Classification Search ............. 340/573.1, 340/573.5, 573.7, 309.3, 309.4, 309.7, 321, 340/323 R; 463/23, 25, 42, 43; 221/2, 25; 368/10
See application file for complete search history.

(56) References Cited

U.S. PATENT DOCUMENTS 3,943,336 A    3/1976   Dillard (Continued)

FOREIGN PATENT DOCUMENTS

EP    0 132 782 A2    2/1985

(Continued)

OTHER PUBLICATIONS

Simmons, Gustavus J., "Proceedings of the 1983 Symposium on Security and Privacy", Sponsored by the Technical Committee on Security and Privacy, IEEE Computer Society, Apr. 25-27, 1983, pp. 61-66, (7pp.).

(Continued)

*Primary Examiner*—Van T. Trieu
(74) *Attorney, Agent, or Firm*—Fincham Downs, LLC

(57) ABSTRACT

According to some embodiments, systems, apparatus, methods, and articles of manufacture may provide for improved health care compliance. Embodiments may comprise, for example, identifying an occurrence of an event associated with the taking of a substance by a patient, determining output information associated with a game, and providing the output information to the patient. Some embodiments may comprise receiving a code associated with a patient, wherein the code includes encoded information that is indicative of an occurrence of an event associated with the taking of a substance by a patient, decoding the code to determine the information, determining whether the occurrence of the event is compliant with a condition associated with the taking of the substance, and providing, in the case that compliance with the condition is determined, one or more rewards to the patient.

36 Claims, 9 Drawing Sheets

U.S. PATENT DOCUMENTS

| | | | |
|---|---|---|---|
| 3,990,558 A | 11/1976 | Ehrat | 194/4 R |
| 4,047,000 A | 9/1977 | Bryant | |
| 4,108,364 A | 8/1978 | Tanaka | |
| 4,123,747 A | 10/1978 | Lancto | |
| 4,223,801 A | 9/1980 | Carlson | |
| 4,253,158 A | 2/1981 | McFiggans | |
| 4,275,384 A | 6/1981 | Hicks | |
| 4,361,408 A | 11/1982 | Wirtschafter | |
| 4,376,299 A | 3/1983 | Rivest | |
| 4,473,884 A | 9/1984 | Behl | |
| 4,526,474 A | 7/1985 | Simon | 368/10 |
| 4,573,606 A | 3/1986 | Lewis | |
| 4,588,303 A | 5/1986 | Wirtschafter et al. | 368/10 |
| 4,616,316 A | 10/1986 | Hanpeter et al. | 364/413 |
| 4,637,051 A | 1/1987 | Clark | |
| 4,641,346 A | 2/1987 | Clark | |
| 4,641,347 A | 2/1987 | Clark | |
| 4,658,093 A | 4/1987 | Hellman | 380/25 |
| 4,660,221 A | 4/1987 | Dlugos | |
| 4,666,160 A | 5/1987 | Hamilton | |
| 4,682,299 A | 7/1987 | McIntosh et al. | 364/569 |
| 4,695,954 A | 9/1987 | Rose et al. | 364/413 |
| 4,766,542 A | 8/1988 | Pilarczyk | |
| 4,768,176 A | 8/1988 | Kehr | |
| 4,768,177 A | 8/1988 | Kehr et al. | 368/10 |
| 4,782,966 A | 11/1988 | Thackrey | 215/230 |
| 4,786,940 A | 11/1988 | Daniele | 355/6 |
| 4,803,625 A | 2/1989 | Fu et al. | 364/413.03 |
| 4,807,287 A | 2/1989 | Tucker | |
| 4,831,438 A | 5/1989 | Bellman, Jr. et al. | 348/148 |
| 4,835,713 A | 5/1989 | Pastor | |
| 4,838,275 A | 6/1989 | Lee | |
| 4,855,580 A | 8/1989 | Van Maanen | |
| 4,856,787 A | 8/1989 | Itkis | |
| 4,899,839 A | 2/1990 | Dessertine et al. | 177/25 |
| 4,926,572 A | 5/1990 | Holmes | |
| 4,939,705 A | 7/1990 | Hamilton et al. | 368/10 |
| 4,971,221 A | 11/1990 | Urquhart et al. | 221/2 |
| 4,972,480 A | 11/1990 | Rosen | |
| 5,001,752 A | 3/1991 | Fischer | 380/23 |
| 5,014,798 A | 5/1991 | Glynn | 177/25.19 |
| 5,016,172 A | 5/1991 | Dessertine | 364/413.02 |
| 5,022,080 A | 6/1991 | Durst et al. | 380/23 |
| 5,027,395 A | 6/1991 | Anderson et al. | 380/4 |
| 5,036,461 A | 7/1991 | Elliott et al. | 364/408 |
| 5,050,212 A | 9/1991 | Dyson | 380/25 |
| 5,073,931 A | 12/1991 | Audebert et al. | 380/23 |
| 5,075,862 A | 12/1991 | Doeberl et al. | 395/117 |
| 5,083,271 A | 1/1992 | Thacher et al. | 364/411 |
| 5,112,051 A | 5/1992 | Darling et al. | 273/148 B |
| 5,136,646 A | 8/1992 | Haber et al. | 380/49 |
| 5,136,647 A | 8/1992 | Haber et al. | 380/49 |
| 5,142,484 A | 8/1992 | Kaufman et al. | 222/638 |
| 5,153,837 A | 10/1992 | Shaffer | |
| 5,155,680 A | 10/1992 | Wiedemer | 364/406 |
| 5,157,726 A | 10/1992 | Merkle et al. | 380/23 |
| 5,189,700 A | 2/1993 | Blandford | 380/23 |
| 5,193,114 A | 3/1993 | Moseley | 380/23 |
| 5,200,891 A | 4/1993 | Kehr | |
| 5,202,923 A | 4/1993 | Kuriyama | 380/50 |
| 5,206,899 A | 4/1993 | Gupta | |
| 5,210,785 A | 5/1993 | Sato | |
| 5,243,652 A | 9/1993 | Teare et al. | 380/21 |
| 5,243,654 A | 9/1993 | Hunter | 380/51 |
| 5,259,029 A | 11/1993 | Duncan, Jr. | 380/4 |
| 5,288,978 A | 2/1994 | Iijima | 235/380 |
| 5,297,205 A | 3/1994 | Audebert et al. | 380/23 |
| 5,298,883 A | 3/1994 | Pilney | |
| 5,299,701 A | 4/1994 | Barker et al. | 215/230 |
| 5,319,710 A | 6/1994 | Atalla et al. | 380/23 |
| 5,333,106 A | 7/1994 | Lanpher | |
| 5,347,579 A | 9/1994 | Blandford | 380/25 |
| 5,347,580 A | 9/1994 | Molva et al. | 380/25 |
| 5,349,642 A | 9/1994 | Kingdon | 380/25 |
| 5,351,293 A | 9/1994 | Michener et al. | 380/21 |
| 5,355,413 A | 10/1994 | Ohno | 380/24 |
| 5,359,510 A | 10/1994 | Sabaliauskas | 364/410 |
| 5,367,573 A | 11/1994 | Quimby | |
| 5,372,276 A | 12/1994 | Daneshvar | 221/2 |
| 5,377,268 A | 12/1994 | Hunter | 380/23 |
| 5,386,468 A | 1/1995 | Akiyama et al. | 380/25 |
| 5,392,952 A | 2/1995 | Bowden | |
| 5,393,057 A | 2/1995 | Marnell | |
| 5,400,319 A | 3/1995 | Fite et al. | 369/275.5 |
| RE34,954 E | 5/1995 | Haber et al. | 380/49 |
| 5,412,575 A | 5/1995 | Constant et al. | 364/464.01 |
| 5,414,841 A | 5/1995 | Bingham | |
| 5,416,840 A | 5/1995 | Cane et al. | 380/4 |
| 5,434,918 A | 7/1995 | Kung et al. | 380/25 |
| 5,448,641 A | 9/1995 | Pintsov | |
| 5,463,547 A | 10/1995 | Markowitz | |
| 5,464,971 A | 11/1995 | Sutcliffe | |
| 5,472,113 A | 12/1995 | Shaw | 221/7 |
| 5,490,217 A | 2/1996 | Wang | |
| 5,497,419 A | 3/1996 | Hill | 380/9 |
| 5,499,249 A | 3/1996 | Agrawal | |
| 5,499,294 A | 3/1996 | Friedman | 380/10 |
| 5,500,897 A | 3/1996 | Hartman, Jr. | |
| 5,508,731 A | 4/1996 | Kohorn | 348/1 |
| 5,539,822 A | 7/1996 | Lett | 380/20 |
| 5,549,117 A | 8/1996 | Tacklind | |
| 5,564,429 A | 10/1996 | Bornn | |
| 5,569,082 A | 10/1996 | Kaye | |
| 5,583,831 A | 12/1996 | Churchill et al. | 368/10 |
| 5,589,838 A | 12/1996 | McEwan | 342/387 |
| 5,600,706 A | 2/1997 | Dunn | |
| 5,623,242 A | 4/1997 | Dawson, Jr. | |
| 5,626,144 A | 5/1997 | Tacklind | |
| 5,638,186 A | 6/1997 | Motoyama | |
| 5,641,091 A | 6/1997 | Daneshvar | 221/3 |
| 5,642,731 A | 7/1997 | Kehr | |
| 5,646,912 A | 7/1997 | Cousin | 368/10 |
| 5,646,994 A | 7/1997 | Hill | 380/9 |
| 5,657,236 A | 8/1997 | Conkright | |
| 5,678,182 A | 10/1997 | Miller | |
| 5,678,571 A | 10/1997 | Brown | 128/898 |
| 5,695,091 A | 12/1997 | Winings | |
| 5,704,366 A | 1/1998 | Tacklind | |
| 5,710,551 A | 1/1998 | Ridgeway | 340/870.09 |
| 5,722,418 A | 3/1998 | Bro | 128/732 |
| 5,752,235 A | 5/1998 | Kehr | |
| 5,757,271 A | 5/1998 | Andrews | |
| 5,758,288 A | 5/1998 | Dunn | |
| 5,761,309 A | 6/1998 | Ohashi | |
| 5,768,382 A | 6/1998 | Schneier et al. | 380/23 |
| 5,774,865 A | 6/1998 | Glynn | 705/2 |
| 5,779,549 A | 7/1998 | Walker et al. | 463/42 |
| 5,794,207 A | 8/1998 | Walker et al. | 705/1 |
| 5,800,264 A | 9/1998 | Pascal et al. | 463/16 |
| 5,828,751 A | 10/1998 | Walker et al. | 380/25 |
| 5,831,859 A | 11/1998 | Medeiros | |
| 5,850,344 A | 12/1998 | Conkright | 364/479.01 |
| 5,850,447 A | 12/1998 | Peyret | 380/25 |
| 5,852,408 A | 12/1998 | Christiansen | |
| 5,852,590 A | 12/1998 | De la Huerga | 368/10 |
| H1782 H | 2/1999 | Wicks | |
| 5,867,821 A | 2/1999 | Ballantyne et al. | 705/2 |
| 5,871,398 A | 2/1999 | Schneier et al. | 463/16 |
| 5,899,998 A | 5/1999 | McGauley | |
| 5,911,132 A | 6/1999 | Sloane | 705/3 |
| 5,913,197 A | 6/1999 | Kameda | |
| 5,923,018 A | 7/1999 | Kameda | |
| 5,923,763 A | 7/1999 | Walker et al. | 380/51 |
| 5,950,630 A | 9/1999 | Portwood | |

| | | | |
|---|---|---|---|
| 5,950,632 A | 9/1999 | Reber et al. ................. 128/898 | |
| 5,954,641 A | 9/1999 | Kehr | |
| 5,960,403 A | 9/1999 | Brown | |
| 5,963,136 A | 10/1999 | O'Brien | |
| 5,969,678 A | 10/1999 | Stewart | |
| 5,970,143 A | 10/1999 | Schneier et al. ............... 380/23 | |
| 6,002,427 A | 12/1999 | Kipust | |
| 6,004,020 A | 12/1999 | Bartur | |
| 6,014,432 A | 1/2000 | Modney | |
| 6,018,289 A | 1/2000 | Sekura | |
| 6,022,315 A | 2/2000 | Iliff | |
| 6,032,085 A | 2/2000 | Laurent | |
| 6,070,761 A | 6/2000 | Bloom | |
| 6,108,685 A | 8/2000 | Kutzik et al. ................. 709/200 | |
| 6,151,586 A | 11/2000 | Brown ......................... 705/14 | |
| 6,167,362 A | 12/2000 | Brown et al. .................. 703/11 | |
| 6,182,219 B1 | 1/2001 | Feldbau | |
| 6,188,766 B1 | 2/2001 | Kocher | |
| 6,198,685 B1 | 3/2001 | Sudo | |
| 6,259,654 B1 | 7/2001 | de la Huerga | |
| 6,294,999 B1 | 9/2001 | Yarin | |
| 6,335,907 B1 | 1/2002 | Momich et al. ............... 368/10 | |
| 6,375,038 B1 | 4/2002 | Daansen | |
| 6,484,027 B1 | 11/2002 | Mauney et al. .............. 455/421 | |
| 6,529,446 B1 | 3/2003 | de la Huerga | |
| 6,689,103 B1 | 2/2004 | Palasis | |
| 6,771,174 B2 | 8/2004 | Broas ...................... 340/573.1 | |
| 7,170,409 B2 | 1/2007 | Ehrensvard et al. .... 340/539.26 | |
| 7,170,823 B2 | 1/2007 | Fabricius et al. .............. 368/10 | |
| 2003/0060286 A1 | 3/2003 | Walker et al. ................. 463/42 | |
| 2008/0077430 A1 | 3/2008 | Singer ........................... 705/2 | |

FOREIGN PATENT DOCUMENTS

| | | |
|---|---|---|
| EP | 0 154 972 A2 | 9/1985 |
| EP | 0 331 352 A2 | 9/1989 |
| EP | 0 440 021 A2 | 8/1991 |
| EP | 0 526 166 A2 | 2/1993 |
| EP | 0526166 A3 | 3/1993 |
| EP | 0547837 A2 | 6/1993 |
| EP | 0684575 | 12/1994 |
| EP | 0727894 A1 | 8/1996 |
| GB | 2 065 030 A | 6/1981 |
| GB | 2240543 A | 8/1991 |
| JP | 03029661 A * | 2/1991 |
| JP | 403256876 A | 11/1991 |
| JP | 7-68051 | 3/1995 |
| JP | 7/068051 | 3/1995 |
| JP | 7/255950 | 10/1995 |
| JP | 7-255950 | 10/1995 |
| WO | WO 95/09386 | 4/1995 |
| WO | WO 95/26009 | 9/1995 |
| WO | WO 00/19962 A2 | 4/2000 |

OTHER PUBLICATIONS

Morris, Daniel C., "The ten basics of system security", Computers in Healthcare, Nov. 1989, Section: vol. 10, No. 11, p. 41, ISSN: 0745-1075, 3pp.

Gardner, Elizabeth, "Computer dilemma: clinical access vs. confidentiality", Modern Healthcare, Nov. 3, 1989, pp. 32-34, 38, 40, 42 (6pp.).

"Monitors compliance; Medi-Monitor programmable medication dispenser; RX: Mass Market Retail Pharmacy", Chain Drug Review, Jul. 30, 1990, Section: vol. 12, No. 21, p. RX8, ISSN: 0164-9914, 2pp.

Brown, Lowell C. et al., "Computerized Patient Records—CPR and the Law: Plan Now", Health Systems Review, Nov./Dec. 1992, vol. 25, Issue 6, ISSN: 1055-7466, 6pp.

Heikens, Norm, "Inventor hopes $2_{nd}$ marketing try on medication monitor is charm", Indianapolis Business Journal, Feb. 1, 1993, Section: vol. 13, No. 45, Sec. 1, p. 11A, 3pp.

Ognibene, Peter J., "'Smart Cards' Could Save Lives-and Dollars Health care: A computerized personal medical record would assist doctors and pharmacists and avert dangerous errors.", The Los Angeles Times, Home Edition, Apr. 12, 1993, Start p. 7, ISSN: 04583035, 2pp.

Amos, Paul J. et al., "Drug cards manage rising prescription costs", Personal Journal, May 1993, vol. 72, Issue 5, ISSN: 0031-5745, 6pp.

Betts, Mitch, "Smart cards lose out in health reform", Computerworld, Feb. 28, 1994, vol. 28, Issue 9, ISSN: 0010-4841, 2pp.

Stevens, Larry, "Taking Your Medicine; Doctors Consider Monitors For Patients Who Can't Keep Track of Prescriptions", St. Louis Post-Dispatch, Aug. 22, 1994, Section: Everyday Magazine, p. 1E, 3pp.

"High-Tech Reminders", St. Louis Post-Dispatch, Aug. 22, 1994, Section: Everyday Magazine, p. 1E, 2pp.

"Patient financial incentives for compliance, feedback suggested by Medco exec; expanded use of questionnaires in disease management programs planned", FDC Reports: The Pink Sheet Sep. 19, 1994, vol. 56, Issue 38, 4pp.

Hussar, Daniel A., "Patient compliance: the ongoing challenge facing pharmacy.", American Druggist, Nov. 1994, Section: vol. 211, No. 1, p. 83, ISSN: 0190-5279, 13pp.

Gannon, Kathi, "Keeping track; new in-home system helps patient stay compliant.", Drug Topics, Feb. 6, 1995, Section: vol. 139, No. 3, p. 60, ISSN: 0012-6616, 2pp.

"Compliance is a phone call away", Med Ad News, Mar. 1995, Section: p. 12, ISSN: 0745-0907, 2pp.

Tashkin, Donald, "Multiple dose regimens: impact on compliance bronchiodilator therapy for chronic obstructive pulmonary disease; supplement", Chest, May 1995, Section: vol. 107, No. 5, p. 176S, ISSN: 0012-3692, 9pp.

Young, David, "Fear Not, Free Enterprise; U.S. Ingenuity Alive and Well", Chicago Tribune, Jun. 26, 1995, Section: Business, p. 3, Zone C, Biz Tips, 1pg.

Press Release: "Fist Fully Authenticated Digital Video Surveillance System Features Advanced RSA Security Technology", RSA Data Security, Inc., Oct. 23, 1995, 2pp.

Schneier, Bruce, "Applied Cryptography, Second Edition—Protocols, Algorithms, and Source Code in C", John Wiley & Sons, Inc., Copyright 1996, Chapter 2, pp. 21-46 (27pp.).

Resnik, W.M., "Technology Track—Digital Image Authentication", Aquila Technologies Group, Inc., Jan. 17, 1996, 7pp.

"Conference Coverage (IUATLD) Simplified Medication Monitor Presented", Tuberculosis & Airborne Disease Weekly, Mar. 17, 1997, 2pp.

"New Line of Telemedical 'Personal Medical Assistants' Will Monitor Patients' Condition and Help Millions Take Prescriptions on Time, In Sequence, and in Proper Dosage", PR Newswire, Apr. 9, 1997, Section: Financial News, 2pp.

Berg, Jill et al., "An evaluation of a self-management program for adults with asthma", Clinical Nursing Research, Aug. 1997, Section: No. 3, vol. 6, p. 225, ISSN: 1054-7738, 14pp.

Corden, Zoe M. et al., "Home nebulized therapy for patients with COPD: patient compliance with treatment and its relation to quality of life; chronic obstructive pulmonary disease", Chest, Nov. 1997, Section: No. 5, vol. 112, p. 1278, ISSN: 0012-3692, 6pp.

"Electronic monitoring gains more acceptance: formerly clunky devices now cheap, user-friendly; devices to track medication compliance", AIDS Alert, Feb. 1998, Section: No. 2, vol. 13, p. 21, ISSN: 0887-0292, 3pp.

Fried, Lisa I., "Annual Report Part 1: Full Integration Within American Stores", Drug Store News, Apr. 27, 1998, p. 145, 6pp.

Trueland, Jennifer, "New Drug Hope For Asthma Sufferers", The Scotsman, Jul. 21, 1998, p. 5, 2pp.

Website: "APREX Clinic-based Patient Compliance/Adherherence", Sep. 14, 1998, 3pp.

Website: "Exact CM Compliance Monitoring System for Clinical Trials", Exact CM, Sep. 14, 1998, 3pp.

Pendrak, Robert F., "Information technologies need to protect patient confidentiality.", Healthcare Financial Management, Oct. 1998, Section: No. 10, vol. 52, p. 66, ISSN: 0735-0732, 4pp.

PCT International Search Report for International Application No. PCT/US 99/21895, now abandoned, in the name of Walker et al., mailed Apr. 19, 2000, 8pp.

Jacobson, Terry A., "The Forgotten Cardiac Risk Factor: Noncompliance With Lipid-Lowering Therapy", Medscape Cardiology, Copyright 2004, Hyperlipidemia Expert Column, l0pp.

Benner, Joshua S. et al., "Association between short-term effectiveness of statins and long-term adherence to lipid-lowering therapy", Am J Health-Syst Pharm, Jul. 15, 2005, vol. 62, Reports, pp. 1468-1475, 8pp.

Giuffrida, Antonio et al. "Should we Pay the Patient? Review of Financial Incentives to Enhance Patient Compliance", Sep. 20, 1997, British Medical Journal, 15 pp.

Rubenstein, Ed. "Operators Squelching Shrinkage with Cutting-Edge Liquor-Management Systems", Oct. 6, 1997, Nation's Restaurant News, 4 pp.

"Mid-Atlantic Tests Monitoring Device for CHF Patients", Oct. 1, 1998, Telehealth Magazine, 2 pp.

"Turning on to Radio", Jan. 14, 1999, Packaging Magazine, 4 pp.

"Virtual Nags: New Devices Track Medication Compliance", Mar. 25, 1999, Medical Outcomes and Guidelines Alert, 2 pp.

Elder, Nina. "A Dose in Time; There are Many Ways to Remember to Take Prescription Medicine; Brief", Jul. 1, 1999, Better Homes and Gardens, 2 pp.

Chin, L. Tyler. "Identifying New Uses for Bar Coding Technology." Aug. 1999. Health Data Management, 6 pp.

"Clever Containers." Sep. 6, 1999. Electronics Times, 3 pp.

Moore, Bert. "How to Identify the Odd Item: From Pistons to Casino Chips, Unique Articles are Getting Tagged with Unique Ideas; Technology Information." Nov. 1, 1999. Automatic I.D. News, 13 pp.

Kaiser, Rob. "New Labels May Replace Bar Codes." Nov. 28, 1999. Las Vegas Review-Journal, 3 pp.

Forger, Gary. "Taking Advantage of RF Technologies for Real-Time Control." Nov. 30, 1999. Modern Materials Handling, 5 pp.

"Catalyst Awarded PE Biosystems' Warehouse Management System Project", PR Newswire (to Business and Technology Editors): Dec. 23, 1999, 2 pp.

"We're Different Because We Are Determined to Make Healthcare Better for You." 1999, Oxford Health Plans, 8 pp.

"Exercise Facility Benefit." Dec. 1996, 3 pp.

Weeks, John. "Charting the Mainstream: Doctor-Patient Communication, Women in Medicine, Pharmaceutical Positioning Under Managed Care, and More. . ." Jan. 1995, 6 pp.

Scott, Miriam Basch. "Disease Management, Touted as the Next Frontier, Aims for Quality Care and Reduced Costs", Dec., 1995, Employee Benefit Plan Review, 7 pp.

"Cap for TB, A Clinic-Based Adherence/Compliance Program for Monitoring Tb Patients" Sep. 14, 1998, 2 pp.

"Quick Read Reveals Compliance Statistics from Each Dispenser", Sep. 14, 1998, 1 pg.

Holcomb, Henry J. "Keeping Tags on Everything: A New Generation of Smart Tags will Allow Merchants to Better Combat Theft and Fraud, and Make Inventory a Breeze. . .", Aug. 3, 1999, National Post, 5 pp.

Trunk, Christopher. "On the Fast Track to Smart Tags. . .", Sep. 1, 1999, Material Handling Engineering, 6 pp.

"The Product" Jan. 26, 2000, 2 pp.

"Electronic Id, Destron Fearing Electronic Identification Microchip", Feb. 2, 2000, 8 pp.

"The Official Bluetooth Website." http://www bluetoothguide com, Feb. 2, 2000, 2 pp.

Freudenheim, Milt, "Corrective Medicine, New Technology Helps Health Care Avoid Mistakes", Feb. 3, 2000, New York Times, 6 pp.

Dalzell, Michael D. "Pharmacy Copayments: A Double-Edged Sword" Feb. 15, 2000, Managed Care Magazine, 9 pp.

"Kumetrix Technology Overview Painless Blood-Gulcose Monitoring", May 18, 2000, Kumetrix.com, 2 pp.

Toon, John. "Taking the Ouch Out of Needles: Arrays of Micron-Scale Microneedles Offer New Technique for Drug Delivery", Jun. 5, 2000, 4 pp.

"Catalyst Awarded PE Biosystems' Warehouse Management System Project", Dec. 23, 1999, PR Newswire, 3 pp.

"Quick Read reveals compliance statistics from each dispenser" Dispensing Times by Position [online] [retrieved on Sep. 14,1998], 1pg.

Kouides et al. "A Performance-based incentive program for influenza immunization in the elderly", Am J Prey Med., 1993, http://www ncbi nlm nih gov/pubmed/8398226, 4 pp.

Coca-Cola, American Express uncork Hawaii vacations contest, http://www highbeam com/doc/1G1-7615573 html, Magenheim, Henry, Travel Weekly, May 25 1989, 2 pp.

Decision on Appeal for U.S. Appl. No. 09/609,017 (00-055), mailed Dec. 6, 2006, 11 pp.

Examiner's Answer to Appeal Brief for U.S. Appl. No. 09/609,017 (00-055) dated Sep. 22, 2004, 51 pp.

Notice of Allowability for U.S. Appl. No. 08/628,920 (95-006), mailed Feb. 20, 1998, 4 pp.

Notice of Allowance for U.S. Appl. No. 09/609,017 (00-055) dated Oct. 15, 2007, 7 pp.

Notice of Allowance for U.S. Appl. No. 10/835,422 (04-006), dated Mar. 11, 2009, 6 pp.

Notice of Allowance for U.S. Appl. No. 11/424,002 (04-006-C1) mailed Feb. 23, 2009, 6 pp.

Notice of Allowance for U.S. Appl. No. 11/424,008 dated Sep. 18, 2009, 7 pp.

Notice of Allowance, U.S. Appl. No. 09/609,017 (00-055), mailed Mar. 21, 2007, 7 pp.

Office Action for U.S. Appl. No. 08/561,668 (95-002), mailed Jun. 6, 1997, 6 pp.

Office Action for U.S. Appl. No. 08/628,920 (95-006), mailed Dec. 22, 1997, 5 pp.

Office Action for U.S. Appl. No. 08/628,920 (95-006), mailed Jul. 23, 1997, 4 pp.

Office Action for U.S. Appl. No. 08/677,544 (95-002X), mailed Apr. 29, 1998, 4 pp.

Office Action for U.S. Appl. No. 09/165,089 (98-051), mailed Feb. 7, 2003, 10 pp.

Office Action for U.S. Appl. No. 09/165,089 (98-051), mailed May 8, 2002, 9 pp.

Office Action for U.S. Appl. No. 09/165,089 (98-051), mailed Mar. 14, 2001, 11 pp.

Office Action for U.S. Appl. No. 09/165,089 (98-051), mailed Jul. 17, 2000, 9 pp.

Office Action for U.S. Appl. No. 09/609,017 (00-055), mailed Aug. 12, 2003, 13 pp.

Office Action for U.S. Appl. No. 09/609,017, mailed Dec. 4, 2002 (00-055), 12 pp.

Office Action for U.S. Appl. No. 09/609,253 (00-007) dated Jan. 30, 2008, 17 pp.

Office Action for U.S. Appl. No. 09/609,253 (00-007) dated May 22, 2006, 2 pp.

Office Action for U.S. Appl. No. 09/609,253 (00-007) dated Jul. 26, 2007, 9 pp.

Office Action for U.S. Appl. No. 09/609,253 (00-007), mailed Jan. 17, 2007, 17 pp.

Office Action for U.S. Appl. No. 09/609,253 (00-007), mailed Jan. 18, 2006, 9 pp.

Office Action for U.S. Appl. No. 09/609,253 (00-007), mailed Dec. 30, 2004, 17 pp.

Office Action for U.S. Appl. No. 09/609,253 (00-007), mailed Mar. 24, 2003, 6 pp.

Office Action for U.S. Appl. No. 09/609,253 (00-007), mailed Apr. 7, 2004, 27 pp.

Office Action for U.S. Appl. No. 09/609,253 (00-007), mailed Jul. 17, 2003, 27 pp.

Office Action for U.S. Appl. No. 10/835,422 (04-006), mailed Mar. 18, 2008, 13 pp.

Office Action for U.S. Appl. No. 10/835,422 (04-006), mailed Sep. 15, 2008, 12 pp.

Office Action for U.S. Appl. No. 11/423,881, (00-007-C1) dated Jan. 9, 2008, 15 pp.

Office Action for U.S. Appl. No. 11/423,881, (00-007-C1) dated Oct. 20, 2008, 11 pp.

Office Action for U.S. Appl. No. 11/423,997 (04-006-C2) dated Aug. 18, 2008, 9 pp.

Office Action for U.S. Appl. No. 11/423,997 (04-006-C2) dated Mar. 18, 2008, 13 pp.
Office Action for U.S. Appl. No. 11/424,002 (04-006-C1) dated Mar. 18, 2008, 12 pp.
Office Action for U.S. Appl. No. 11/424,002 (04-006-C1) dated Aug. 22, 2008, 6 pp.
Office Action for U.S. Appl. No. 11/424,008 dated Mar. 18, 2008, 14 pp.
Office Action for U.S. Appl. No. 11/424,008 dated Aug. 22, 2008, 13 pp.
PCT/US2005/014829 Int'l Search Report Dec. 2007, 6 pp.
Notice of Allowance for U.S. Appl. No. 11/423,997 (04-006-C2) dated Aug. 28, 2009, 7 pp.
Office Action for U.S. Appl. No. 09/149,025 (95-006X) dated Jul. 7, 1999, 5 pp.
Office Action for U.S. Appl. No. 09/149,025 (95-006X) dated Feb. 1, 2000, 5 pp.
Notice of Allowability for U.S. Appl. No. 09/706,646 (95-006XX) dated Mar. 13, 2001, 5 pp.

* cited by examiner

← 430

| EVENT_ID 430-1 | EVENT_TYPE 430-2 | EVENT_TIME 430-3 |
|---|---|---|
| 001 | CAP_OPEN | 08/29/2005 0918.43 |
| 002 | CAP_CLOSED | 08/29/2005 0918.52 |
| AD83M CL8 | PATCH_APPLIED | 04/29/2005 2300.01 |

| CONDITION_ID 432-1 | CONDITION_TYPE 432-2 | CONDITION_DESCRIPTION 432-3 |
|---|---|---|
| C-0100 | PRESCRIPTION | ONE PILL DAILY |
| C-0101 | RECOMMENDED | TAKE BETWEEN 0800 AND 0900 |
| SMITH04529 | DIETARY | 4 OZ. FIBER WITH EACH MEAL |

| GAME_ID 434-1 | GAME_NAME 434-2 | GAME_DATA1 434-3 | GAME_DATA2 434-4 |
|---|---|---|---|
| 001 | BINGO | B 25 | N 13 |
| 002 | LOTTO | 6 17 22 27 35 37 | 2 39 1 5 17 21 |
| 459 | MINESWEEPER | E 9 | C 4 |

| COMPLIANCE_MODULE_ID 1070-1 | PATIENT_ID 1070-2 | KEY 1070-3 |
|---|---|---|
| CP-43130-92-45-X | SMITH_J_945 | 100100110 110110 |
| CP-43130-93-10-X | 2385764 | 110111100 111110 |
| CP-43130-99-00-D | PAFHJ73F | 101101100 010100 |

| PATIENT_ID 1072-1 | PHONE 1072-2 | INSURANCE_ID 1072-3 | CONDITION_ID 1072-4 | TAMPER 1072-5 | SCORE 1072-6 | RANK 1072-7 |
|---|---|---|---|---|---|---|
| DOE_BOB | 456-7890 | CIGNA_9384 | C-0100 | N | 546 | 1 |
| 872 | 765-4321 | BCBS_237 | C-0101 | Y | 238 | 2 |
| JANE_93B | 001-9342 | OXFORD_9273 | C-0101 | N | 67 | 3 |

| GAME_ID 1074-1 | GAME_NAME 1074-2 | WIN_CODE 1074-3 | PRIZE 1074-4 |
|---|---|---|---|
| 001 | BINGO | E239F | NEW CAR |
| 002 | POKER | ACE93 | $100 |
| 459 | MINESWEEPER | 00001 | DISCOUNT |

FIG. 10C

SYSTEMS AND METHODS FOR IMPROVED HEALTH CARE COMPLIANCE

CROSS-REFERENCE TO RELATED CORRESPONDING APPLICATIONS

This application is a continuation of U.S. patent application Ser. No. 11/255,240, filed Oct. 20, 2005, entitled "SYSTEMS AND METHODS FOR IMPROVED HEALTH CARE COMPLIANCE";

which is a continuation-in-part that claims priority and benefit under 35 U.S.C. §120 to commonly owned, U.S. patent application Ser. No. 10/835,422 entitled "METHOD AND APPARATUS FOR OUTPUTTING A RESULT OF A GAME VIA A CONTAINER" filed Apr. 29, 2004 and issued as U.S. Pat. No. 7,553,234 on Jun. 30, 2009, which is a continuation-in-part of U.S. patent application Ser. No. 09/165,089 entitled "METHOD AND APPARATUS FOR DOCUMENTING CAP REMOVAL DATA" filed Oct. 1, 1998, which issued as U.S. Pat. No. 6,751,730 on Jun. 15, 2004.

Each of the above-referenced applications is incorporated by reference herein in its entirety.

BACKGROUND OF THE INVENTION

A major problem facing the health care industry today is the difficulty of enforcing patient compliance with prescription and health care regimens and therapies. All too often, patients ignore the directions associated with their prescriptions, consuming more or fewer pills than recommended by their doctor. Many patients simply forget to take the medication for one or more days, resulting in a lengthened healing process. Adherence to prescriptions for the treatment of asymptomatic conditions is particularly troublesome. Without being reminded of the long-term benefits of a treatment, for example, patients may stop taking a medication when no immediate benefit is apparent (e.g., decreased pain or remediation of another obvious symptom).

In some cases not taking pills according to a precise schedule can result in complications requiring expensive hospital stays or increased time consulting with a physician. Patients taking lipid-lowering medications (e.g., to lower cholesterol) may, for example, experience "excess morbidity and mortality" due to noncompliance with prescription regimens. Jacobsen, Terry A., M.D., "The Forgotten Risk Factor: Noncompliance With Lipid-Lowering Therapy", Medscape® Cardiology, www.medscape.com/viewarticle/496144, posted Dec. 22, 2004, at pg. 7.

Indeed, recent studies have shown that as little as forty to fifty percent (40-50%) of patients taking 3-hydroxymethyl-glutaryl-coenzyme inhibitors ("statins"; e.g., Lipitor®) to lower cholesterol were adhering to their prescriptions after just six (6) months. See, Benner, Joshua S, et al., "Association between short-term effectiveness of statins and long-term adherence to lipid-lowering therapy", Am J Health-Syst Pharm—Vol 62, Jul. 15, 2005. The additional costs due to such noncompliance are passed on to health care providers and insurers. Estimates are that such costs may be in excess of one hundred billion dollars ($100 billion) per year. Jacobsen, at pg. 1.

Efforts to promote increased compliance with health care prescriptions and therapies include "[u]sing a warm and caring tone featuring more positive than negative words," reducing the complexity of treatment regimens, following up with patients that miss appointments, providing e-mail reminders to patients, increasing patient education, and providing reminder, cognitive, and/or self-monitoring aids. Jacobsen, at pg. 6. Such basic tactics have, however, "proved to be complex, labor intensive, and of unreliable effectiveness." Id., at pg. 5. More advanced approaches and methods have also been presented.

One such approach to solving the problem of patient compliance has been the development of modified pill containers that automatically dispense the correct number of pills. U.S. Pat. No. 5,641,091 to Daneshvar describes a medication-dispensing device that allows a patient to receive his medication on a regular basis. A series of small spaces are arranged in one or more electrically powered rotating trays to allow a proper dose via a window. While this approach makes it easier for a conscientious patient to follow his prescription, forgetful patients may simply let pills "build up" rather than consuming them. Additionally, such devices contain many moving parts that are subject to malfunction and wear. Malfunctions could result in legal liability if the patient was provided access to fewer pills than required by his prescription.

A similar dispensing device is described in U.S. Pat. No. 5,472,113 to Shaw. The automatic pill-dispensing device of Shaw has cartridges rotated via an electric motor, electromagnetic clutches, a rotatable shaft, and gears. As with the Daneshvar device, there is no way for a remote third party to know whether or not the device is operating properly and whether the patient is in fact complying with his prescription.

Because third parties such as hospitals and insurance companies would like to have access to patient prescription compliance data, other devices have been created to store data such as how often a pill container has been opened or the time and date that it was opened. U.S. Pat. No. 5,016,172 to Dessertine and U.S. Pat. No. 4,939,705 to Hamilton et al. both describe such an apparatus. These devices, however, either require the user to physically deliver the apparatus to the interested third party for data retrieval and verification, or require that the device have a modem for online connection to the third party. Physical delivery is time consuming and potentially costly for the user, while an online connection requires expensive hardware and greater sophistication on the part of the user.

A need therefore exists for systems, apparatus, methods, and articles of manufacture that address these and other deficiencies of the prior art. A need exists, for example, for securely measuring, reporting, and tracking patient compliance in an off-line environment. A need also exists for facilitating improved patient compliance with health care regimens.

BRIEF DESCRIPTION OF THE DRAWINGS

An understanding of embodiments described herein and many of the attendant advantages thereof may be readily obtained by reference to the following detailed description when considered with the accompanying drawings, wherein:

FIG. 4A, FIG. 4B, and FIG. 4C are block diagrams of data tables according to some embodiments;

FIG. 10A, FIG. 10B, and FIG. 10C are block diagrams of data tables according to some embodiments.

DETAILED DESCRIPTION

Figure 1:
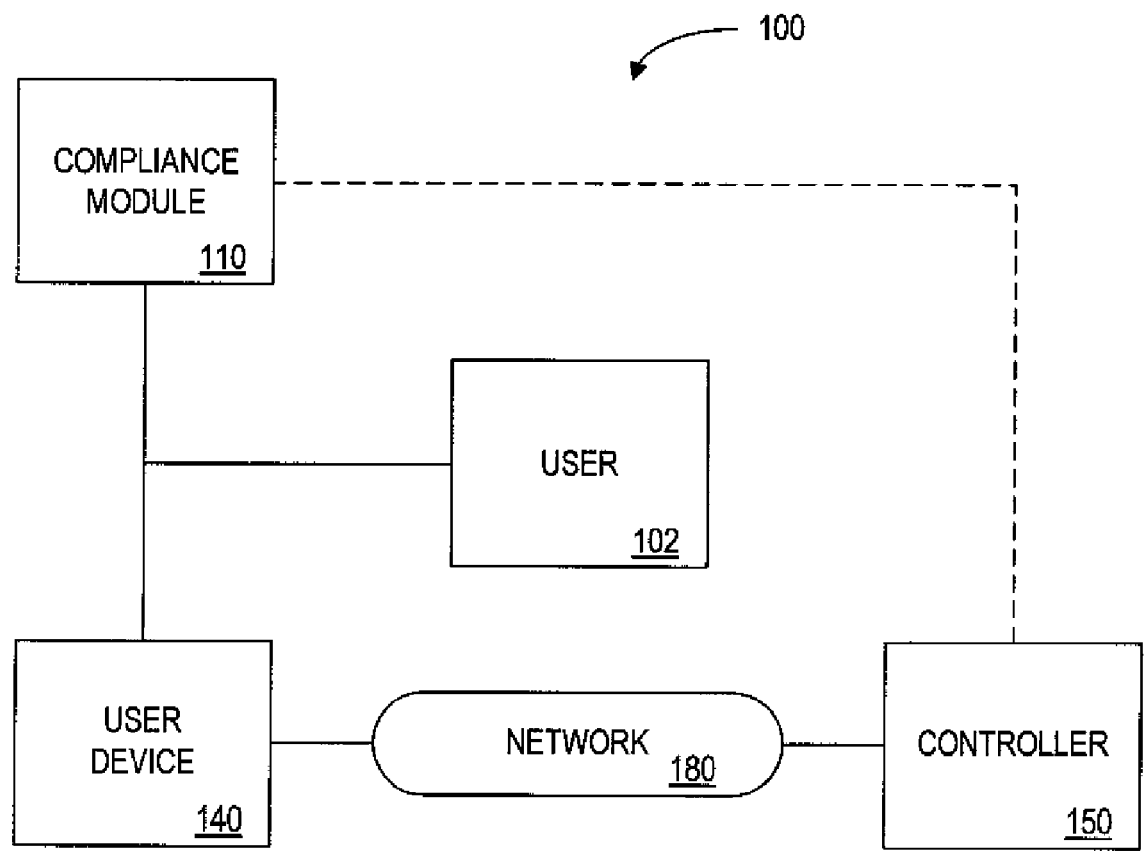
FIG. 1 is a block diagram of a system according to some embodiments.

Some embodiments described herein generally relate to medicine containers, medicine applicators, medicine dispensers, medical equipment, prescription medications, health care regimens or therapies, and methods for improving compliance with prescriptions and health care regimens or therapies. More particularly, some embodiments relate to systems and methods for documenting and authenticating patient compliance with health care regimens, and some embodiments facilitate improvement of patient compliance.

TERMS AND DEFINITIONS

Some embodiments described herein are associated with a "patient". As used herein, the term "patient" may generally refer to any individual, entity, or other being associated with a prescription, therapy, or other health care regimen. Patients may, for example, be persons seeking and/or obtaining preventative, therapeutic, and/or remedial health care treatment.

As used herein, the terms "prescription", "therapy", "regimen", and "health care regimen" may be used interchangeably and may generally refer to any plan, strategy, requirement, treatment, and/or other condition, procedure, or act associated with the health of a patient. Prescriptions may be oral and/or written by a health care professional, for example, and filled by the patient to obtain medications, pills, vitamins, dietary supplements, and/or other health-related devices, objects, or substances.

As used herein, the terms "substance" may generally refer to any quantity or amount of a health-related material that may be depleted, expended, and/or otherwise utilized via the effectuation of a prescription, therapy, or regimen. Examples of some such substances may include, but are not limited to, pills, liquid medications, foods, drinks, ointments, patch-applied medications, inhalants, test strips, and batteries for health care devices. According to some embodiments, the "taking" of a substance may refer to the ingestion (e.g., by a patient) of a pill or medication, the application of a medicated patch, and/or the depletion of a medication or battery (or other energy source) associated with a medical, treatment, therapeutic, and/or exercise device.

In addition, some embodiments herein are associated with "compliance" or "adherence" to, or "acceptance" of, a prescription, therapy, or other health care regimen. As used herein, the terms "compliance", "adherence", and "acceptance" may be used interchangeably to refer to an extent to which a patient's actions coincide with those actions specified by and/or associated with the prescription, therapy, and/or other health care regimen. In some embodiments, compliance may be a dichotomous or Boolean value (e.g., true or false; compliant or noncompliant), while in other embodiments compliance may comprise a continuum. Different patients may, for example, be more or less compliant than others. Patients may also or alternatively be grouped according to one or more compliance variables. The percentage of time that a patient takes the appropriate doses and/or the frequency or magnitude of compliance with dosage schedules may, for example, be utilized to develop or define ranges of values within which patients may be grouped or classified (i.e., in terms of compliance).

Some embodiments described herein are associated with a "user device" or a "network device". As used herein, the terms "user device" and "network device" may be used interchangeably and may generally refer to any device that can communicate via a network. Examples of user or network devices include a Personal Computer (PC), a workstation, a server, a printer, a scanner, a facsimile machine, a copier, a Personal Digital Assistant (PDA), a storage device (e.g., a disk drive), a hub, a router, a switch, and a modem, a video game console, or a wireless phone. User and network devices may comprise one or more communication or network components.

As used herein, the term "network component" may refer to a user or network device, or a component, piece, portion, or combination of user or network devices. Examples of network components may include a Static Random Access Memory (SRAM) device or module, a network processor, and a network communication path, connection, port, or cable.

In addition, some embodiments are associated with a "network" or a "communication network". As used herein, the terms "network" and "communication network" may be used interchangeably and may refer to any object, entity, component, device, and/or any combination thereof that permits, facilitates, and/or otherwise contributes to or is associated with the transmission of messages, packets, signals, and/or other forms of information between and/or within one or more network devices. Networks may be or include a plurality of interconnected network devices. In some embodiments, networks may be hard-wired, wireless, virtual, neural, and/or any other configuration of type that is or becomes known. Communication networks may include, for example, one or more networks configured to operate in accordance with the Fast Ethernet LAN transmission standard 802.3-2002® published by the Institute of Electrical and Electronics Engineers (IEEE). In some embodiments, a network may include one or more wired and/or wireless networks operated in accordance with any communication standard or protocol that is or becomes known or practicable.

As used herein, the terms "information" and "data" may be used interchangeably and may refer to any data, text, voice, video, image, message, bit packet, pulse, tone, waveform, and/or other type or configuration of signal and/or information. Information may comprise information packets transmitted, for example, in accordance with the Internet Protocol Version 6 (IPv6) standard as defined by "Internet Protocol Version 6 (IPv6) Specification" RFC 1883, published by the Internet Engineering Task Force (IETF), Network Working Group, S. Deering et al. (December 1995). Information may, according to some embodiments, be compressed, encoded, encrypted, and/or otherwise packaged or manipulated in accordance with any method that is or becomes known or practicable.

In addition, some embodiments described herein are associated with an "indication". As used herein, the term "indication" may be used to refer to any indicia and/or other information indicative of or associated with a subject, item, entity, and/or other object and/or idea. As used herein, the phrases "information indicative of" and "indicia" may be used to refer to any information that represents, describes, and/or is otherwise associated with a related entity, subject, or object. Indicia of information may include, for example, a code, a reference, a link, a signal, an identifier, and/or any combination thereof and/or any other informative representation associated with the information. In some embodiments, indicia of information (or indicative of the information) may be or include the information itself and/or any portion or component of the information. In some embodiments, an indication may include a request, a solicitation, a broadcast, and/or any other form of information gathering and/or dissemination.

System Architecture

Referring first to FIG. 1, a block diagram of a system 100 according to some embodiments is shown. The various system described herein are depicted for use in explanation, but not limitation, of described embodiments. Different types, layouts, quantities, and configurations of systems described herein may be used without deviating from the scope of some embodiments.

The system 100 may comprise and/or be associated with, for example, a user 102, a compliance module 110, a user device 140, a controller 150, and/or a network 180. In some embodiments, the compliance module 120 may be configured to identify, detect, measure, determine, and/or encode indications of health care-related events associated with the user 102. The compliance module 110 may, for example, detect pill bottle cap removals, movements of a pill bottle, dispensing of a liquid, application of a medicated patch, use of a therapeutic and/or exercise device, removal of a pill from a blister pack, and/or other prescription, therapy, and/or health care regimen-related events. The compliance module 110 may also or alternatively, according to some embodiments, be configured to provide game-related information to the user 102. The user 102 may be motivated to take a medication and/or to more closely adhere to a regimen, for example, by receiving game-related (and/or other motivational) information via the compliance module 110.

In some embodiments, the event data associated with the user 102 may be encoded and/or encrypted by the compliance module 110 and a resulting code and/or information may be provided to the user 102. The user 102 may then, for example, utilize the user device 140 to communicate the code or information (e.g., encoded information indicative of the health care-related event) to the controller 150 (e.g., via the network 180). The user device 140 may, according to some embodiments, be any type or configuration of network device that is or becomes known or practicable. The user device 140 may, for example, comprise a telephone (e.g., wired or wireless) and/or other communication device associated with the user 102.

The controller 150 may, according to some embodiments, utilize the encoded and/or encrypted information to determine if the user 102 is compliant with a prescription, therapy, and/or other health care regimen. The user 102 may, for example, be a patient, and/or the controller 150 may be owned, operated by, and/or otherwise associated with a health care provider, an insurance carrier, an employer, and/or another entity (e.g., a government agency or health department). The controller 150 may also or alternatively receive game-related information from the user 102 (e.g., provided to the user 102 by the compliance module 110). The controller 150 may, for example, utilize either or both of the compliance or game-related information, to provide one or more rewards to the user 102. According to some embodiments, the compliance module 110 may also or alternatively be in communication with the controller 150 (e.g., to provide a code and/or compliance-indicative information, and/or to receive information such as prescription information or software or firmware updates).

In some embodiments, the compliance module 110 may include elements (such as electronic elements) incorporated within the cap of a prescription medication, food, or drink container, although it could also or alternatively take the form of an add-on module coupled or attached to either the container cap or the container itself. The compliance module 110 may be used in conjunction with a pill-dispensing device that is operated to vend pills. A system capable of holding a plurality of prescriptions could also incorporate the functionality of the compliance module 110. In some embodiments, the compliance module 110 may be or include a device that does not dispense or contain a prescription and/or other substances. The compliance module 110 may, for example, comprise a pressure-sensitive pad upon which medicine containers are placed or a medical identification bracelet and/or other device capable of electronically detecting or sensing health care-related substances, containers, or other associated apparatus. According to some embodiments, the compliance module 110 may comprise and/or be coupled to an exercise device (such as a treadmill) to monitor a patients exercise routines and/or health-related metrics (e.g., heart rate).

In operation according to some embodiments, a user 102 may employ the compliance module 110 to measure and document the number of times that an openable or reclosable cap, lid, or other similar dispensing covering is removed from an associated substance container. The container may be equipped, for example, with a detector that generates a first electrical signal in response to the opening of the dispensing covering and also or alternatively a second electrical signal in response to the reclosing.

In accessing the container by removing or replacing the cap, the user 102 may cause cap removal data to be generated and the data may be stored as a numeric value (e.g., via the compliance module 110 and/or components thereof. This cap removal data may be (or be indicative of the total number of times that the cap is removed in a given time period, the number of days in which the cap is removed more than once, the number of days in which the cap is not removed, the average number of removals per day, etc. It should be noted that the same measures may apply equally to cap replacement data which is similar to cap removal data in that both indicate the number of times that a container is accessed. In addition to recording the quantity of removals, compliance module 110 may store chronographic data regarding the timing of the removals. Such chronographic data may include the date/time of each removal, the average time of day of all removals over a particular period, the average number of hours between each removal, etc. The compliance module 110 may receive the cap removal data from cap removal sensors, and may encode the data, thereby generating encoded cap removal data. In some embodiments, the encoded cap removal data may comprise an encoded version of the cap removal data, while in other embodiments, it may additionally incorporate a user identifier, drug identifying data, a cap identifier, an insurance policy identifier and/or other pertinent information such as biometric data or a timestamp.

In some embodiments, the compliance module 110 may display a code or information to the user 102. The code or information may, for example, be associated with game output provided as an incentive to facilitate improved compliance with a prescription and/or may comprise data indicative of one or more prescription-related events (e.g., cap removals and/or other medication or health care-related events). Such information and/or encoded data may take any form that is or becomes practicable, such as a series of numeric digits, symbols, or alphanumeric characters/digits. For example, the user 102 may view a ten-digit number representing the encoded data and enter these digits into an input device associated with the user device 140. The input device may, for example, comprise a keypad of a telephone user device 140 that the user 102 may utilize to communicate via the network 180 (such as a Public Switched Telephone Network (PSTN)) with and Interactive Voice Response Unit (IVRU) associated with the controller 150. The user 102 may also or alternatively read out the digits of the encoded data to a human operator or otherwise communicate the data to the controller 150.

The controller 150 may, according to some embodiments, decode the received encoded data and store the resulting decoded information. In some embodiments, an entity (such as a health care-related entity) may employ the controller 150 to determine and authenticate health care-related actions taken by the user 102. The number of times that the user 102 removes the cap of a pill bottle, for example, may be determined via the encoded information, thereby providing greater assurance that the user 102 has consumed a prescribed medication. Such compliance data may be used to lower insurance premiums in much the same way that motorists are rewarded with lower car insurance premiums for wearing safety belts.

The controller 150 may also or alternatively decode and/or receive the information to determine actions associated with one or more games. Patients determined to meet certain compliance criteria, for example, may be entered into sweepstakes, lotteries, and/or other games of chance or skill. The controller 150 may, for example, provide a compliant patient with one or more lottery tickets or numbers as a reward for attaining compliance. In some embodiments, such as in the case that the information generated by the compliance module 110 comprises game-related information (such as game output intended to promote improved compliance), the controller 150 may analyze and/or otherwise process the information to determine one or more actions or results associated with a game. A patient may, for example, provide the controller 150 with information (which may be encoded) that indicates that the patient has won a game or prize. In some embodiments, the controller 150 may award and/or provide a prize to the patient. According to some embodiments, compliance and/or game information from multiple patients may be compared. Patients belonging to and/or assigned to certain groups (e.g., members of the same health insurance group, members of the same company, and/or residents of the same assisted living facility) may be ranked, for example, to determine which patients should be awarded prizes and/or benefits (e.g., based on compliance and/or game results).

Compliance Module Method

Figure 2:
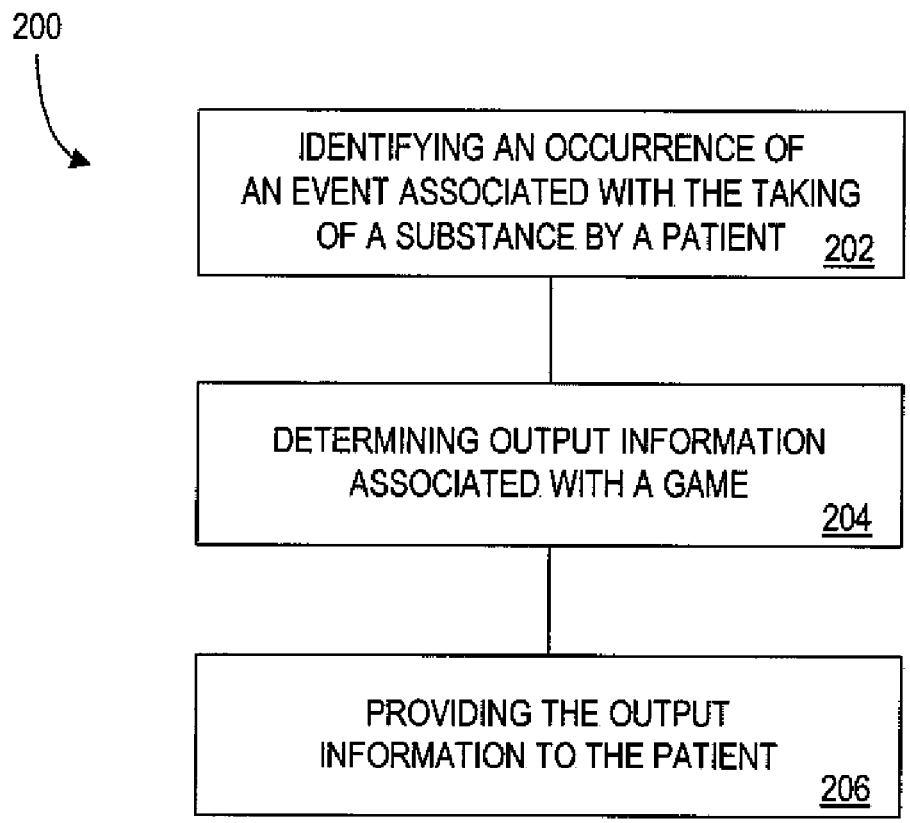
FIG. 2 is a flow diagram of a method according to some embodiments.

Referring now to FIG. 2, a flow diagram of a method 200 according to some embodiments is shown. In some embodiments, the method 200 may be performed and/or implemented by and/or otherwise associated with the compliance module 120 described in conjunction with FIG. 1. The flow diagrams described herein do not necessarily imply a fixed order to the actions, and embodiments may be performed in any order that is practicable. Note that any of the methods described herein may be performed by hardware, software (including microcode), firmware, or any combination thereof. For example, a storage medium may store thereon instructions that when executed by a machine result in performance according to any of the embodiments described herein.

According to some embodiments, the method 200 may begin by identifying an occurrence of an event associated with the taking of a substance by a patient, at 202. The compliance module 120 may, for example, accumulate and/or store data indicating that the cap of a container has been removed (e.g., the cap of a prescription medication bottle or a lid to a dietary supplement container). In some embodiments, such data may be received via signals from a sensor such as a switch that is physically engaged (and/or a circuit that is otherwise opened or closed) when the container cap is removed or replaced. Sensors may generate data for either or both of removals and replacements. According to some embodiments, this data may be stored in one or more data tables as are described in more detail elsewhere herein. In some embodiments, data regarding every cap removal and/or other event may be stored, although data could of course be selectively stored if memory limitations are a constraint. For example, every fifth cap removal and/or other event may be stored and/or every cap removal and/or event occurring during certain pre-defined time periods (e.g., between the hours of 2:00 PM and 6:00 PM) may be stored.

According to some embodiments, other event occurrences may also or alternatively be identified, detected, and/or otherwise determined. In the case that a prescription medication and/or other substance is secured inside of a blister pack, for example, an event may be indicated by the breaking of a seal to remove one or more units of the substance. In some embodiments, the removal of an adhesive backing cover of a medicated patch (such as a Nicotrol® or NicoDerm® nicotine patch) may also or alternatively define such an event. According to some embodiments, the actual usage, ingestion, and/or other application of the substance may be determined. In the case of a patch-administered medication, for example, signals may be sent and/or received (e.g., via the patient's body) to determine that the medicated patch has been applied to the patients skin.

The compliance module 110 may, for example, comprise a medical information bracelet, tag, and/or device (such as a MedicAlert® bracelet or E-HealthKey™) that may detect signals sent through and/or via a patient's body (e.g., indicating application of a medicated patch and/or ingestion or application of a medication). In some embodiments, the compliance module 110 may comprise a necklace, earring, and/or other device capable of detecting proximity of a pill. Each pill to be taken by a patient may, for example, be coupled with a Radio Frequency IDentification (RFID) device that a compliance necklace may detect upon swallowing by a patient. According to some embodiments, the RFID device on the pill may only be activated upon exposure to saliva so that false swallow indications may be less likely.

According to some embodiments, a patient may be supplied with more than one compliance device and/or more than one potential compliance device so that the patient may be less likely to be able to falsify compliance data. A patient may be supplied with a compliance-tracking pill bottle (and/or cap) as well as a compliance-tracking bracelet, for example. In some embodiments, both compliance devices may record and track events and the data may be compared to verify accuracy, identify errors, and/or discover tampering efforts. According to some embodiments, tracking may be alternated (e.g., randomly and/or in accordance with a pre-defined pattern) between the devices, so that the patient may not be aware which device is actively tracking compliance data at any given time.

In some embodiments, movement, proximity, and/or other metrics associated with a substance and/or substance container may be determined. A pressure-sensitive pad (such as a "compliance pad" as described herein) may, for example, be utilized to determine if a container is picked-up, moved, and/or if a quantity of a substance has been removed from the container (e.g., such as in the case that the pad may be capable of detecting or measuring mass, weight, or other forces or metrics).

In some embodiments, a sensor and/or circuit may be utilized to detect the immersion of a syringe into a particular substance. The immersion may, for example, complete a circuit and/or alter a voltage or resistance/impedance in a particularly pre-defined manner that indicates immersion into a substance having certain properties. According to some embodiments, an accelerometer and/or other sensor may detect pill bottle cap removals and/or movements, and/or may detect the shaking of a vial (e.g., which may be required prior to ingestion of a medication contained therein).

In some embodiments, compliance with a condition associated with the taking of the substance may be determined and/or analyzed. Whether an identified event occurrence is compliant with, satisfies (and/or partially satisfies), and/or is otherwise associated with a condition such as a prescription, therapy, and/or regimen condition, may, for example, be determined (e.g., by the compliance module 110 and/or by another device or entity). In some embodiments, an indication of such compliance may be generated and/or stored. The indication may, for example, be indicative of whether or not a condition associated with the taking of the substance is satisfied and/or complied with. Cap removal data may, for example, represent an indication of whether or not a container cap is removed within the parameters described by a prescription. A stored indication of such an event may, according to some embodiments, comprise a positive value in the case that the patient removes the cap once every day between the hours of 3:00 PM and 9:00 PM, and may comprise a negative value in the case that one or more days elapse in which the cap is not removed within the appropriate time window. Any other values (such as values indicating partial compliance) that are or become practicable may also or alternatively be generated and/or stored.

In some embodiments, an indication of the compliance status may be provided to the patient and/or to another entity. The patient may, for example, press a button on the compliance module 110 to indicate a request for the current compliance status. The status may then be indicated to the patient, for example, via one or more displays, sounds, and/or visual indicators (e.g., lights). According to some embodiments, one or more Light-Emitting Diode (LED) devices may be utilized to indicate the current compliance status. A green LED may indicate compliance, for example, while a red LED may indicate non-compliance. In some embodiments, such as in the case that compliance is determined in accordance with a continuum, a yellow or orange LED may indicate partial compliance and/or near non-compliance. In some embodiments, a value of a compliance metric may be provided (e.g., via voice, sounds, and/or via a display device), The text "90%" may, for example, be displayed to the patient to indicate that the patient is currently ninety percent compliant (e.g., with respect to when, how often, how much, and/or which medications or other substances have been taken).

In some embodiments, the compliance module 110 may actively provide an indication of compliance to the patient. In the case that the compliance module 110 comprises a device capable of receiving signals from a heart rate monitor, for example, the compliance module 110 may provide indications to the patient associated with the patient's current heart rate (e.g., during exercise). According to some embodiments, the compliance module 110 may also or alternatively act to affect the patient's heart rate and/or other compliance-related metric, such as by altering the difficulty, slope, and/or speed of a treadmill to actively tailor the patient's workout to comply with one or more health care and/or exercise regimens (with or without the patients knowledge or awareness). In some embodiments, the provided indication may also represent other data. A patient may press a button to receive an indication as to the status of a game, for example.

The method 200 may continue, according to some embodiments, by determining output information associated with a game, at 204. The output may be determined, for example, to facilitate improved compliance with a patient's prescription regimen. According to some embodiments, the output may be determined based on a prescription regimen. In the case that a patient is supposed to take a pill every day between 4:00 PM and 6:00 PM (e.g., with dinner), for example, the game output may be determined to coincide with the prescription window (e.g., may be determined, near, and/or before 4:00 PM). In some embodiments, the output may be determined based on the occurrence of the event (and/or the identification of the occurrence). Every time a patient opens a container associated with a substance, for example, the output may be generated and/or otherwise determined According to some embodiments, the output may be determined only in the case that the occurrence of the event is in compliance with the prescription. It may not be desirable, for example, to determine game output unless a patients actions are in conformance with a health care regimen.

In some embodiments, the output may comprise a code that may be determined to be indicative of the occurrence of the event. The code indicative of the event may, for example, be coded and/or encrypted to resemble a form of game output such as a bingo number, a lottery number, and/or any other type or form of code, coordinate, and/or game-related data. In some embodiments, such a code may be utilized both to indicate compliance (or noncompliance) with a prescription and to determine one or more actions or outcomes related to a game. According to some embodiments, codes generated to be indicative of non-compliant events may be utilized and/or effective as "losing" and/or otherwise negative result-oriented game output, for example, while codes indicative of compliant events may be utilized and/or effective as "winning" and/or positive result-oriented games output. In such a manner, for example, patients that are compliant may be more likely to win a game (e.g., associated with the compliance module 110), while non-compliant (and/or less compliant) patients may be less likely to achieve positive game results. In some embodiments, the compliance module 110 may be provided with information associated with a game (such as the layout of a bingo, minesweeper, and/or battleship board) to facilitate generation of "winning" and/or "losing" game outputs.

According to some embodiments, the amount, quantity, and/or type of game output may also or alternatively be based on the occurrence of the event and/or an associated prescription. In some embodiments, the probability of achieving a winning result via the game output may be based on a patient's compliance. More compliant patients may be entered into a first, smaller drawing or sweepstakes, for example, providing each such compliant patient with relatively high chances of winning. While less compliant patients may be entered into a second, larger drawing or sweepstakes, providing each such patient with larger (or worse) odds of achieving a winning result. Payout tables and/or other metrics utilized to determine the game output may also or alternatively be managed, manipulated, and/or altered based on a patient's compliance.

In some embodiments, the quantity of game output may be managed. In the case that the game output comprises one or more bingo numbers, for example, more bingo numbers may be provided to patients achieving higher compliance, while non-compliant and/or minimally compliant patients may not receive any bingo numbers. In some embodiments, the quantity of game output may be varied in accordance with one or more prescription frequencies. In the case that only one bingo number is provided every time a patient takes a pill, for example, even among patients of equal compliance, those patients with higher frequency prescription doses may have an advantage (e.g., receiving more game output may increase chances of winning). Patients required to take a pill every day may receive thirty (30) bingo numbers a month, for example, while patients only required to take a pill once a week may only receive four (4) bingo numbers a month. In order to manipulate, equalize, standardize, and/or otherwise determine the quantity of game output, according to some embodiments, a desirable amount of output per time period may be determined. In the case that it may be desirable for all patients of equivalent compliance (e.g., in the same compliance group) to receive thirty (30) bingo numbers per month, for example, the amount of game output to be determined may be calculated by the following formula:

$$G=T/n$$

where "G" is the quantity of game output (e.g., such as bingo or other numbers or codes), "T" is the total desired quantity of game output for a given time period, and "n" is the number of times a prescription, therapy, and/or other health care regimen event is to occur during the time period.

The method 200 may continue, according to some embodiments, by providing the output information to the patient, at 206. The game output determined at 204, for example, may be displayed, transmitted, and/or otherwise provided to the patient. According to some embodiments, a subset of the game output determined at 204 may be provided to the patient. In the case that the game information is determined every time an event (such as the opening of a pill bottle) is detected, for example, the game output may only be provided to the patient if the event is determined to be in compliance with a prescription. This may prevent, for example, a patient from obtaining more game output by simply opening and closing a pill bottle repeatedly, when not required to do so by a prescription. In some embodiments, particular game output that is determined at 204 may be selected for providing to the patient. Multiple game output may be determined for various circumstances such as compliance, partial compliance, or non-compliance, for example, and based on a determination of a patients compliance, the corresponding and/or appropriate game output may be selected to be provided to the patient.

According to some embodiments, the output information may be directly displayed to the patient. The compliance module 110 may, for example, comprise a display device capable of providing images and/or other data to the patient. Any code or other game or compliance-related information may be displayed via such a device for viewing by the patient. The output may also or alternatively be transmitted to one or more other devices. One or more devices associated with the patient (such as the user device 140) may, for example, receive the output. Such devices may include, but are not limited to, a computer, a PDA, a watch, a TV, a telephone, a pager, and/or any combination of these and/or other device associated with the patient. The patient may then utilize the device to provide the information to a system (such as the controller 150) and/or other entity that may provide rewards to the patient based at least in part on the patient's compliance and/or upon the game output. According to some embodiments, the output may be otherwise provided to the patient. The output may be spoken, sounded, and/or provided via blinking lights and/or other indicators, for example. In some embodiments, the output may comprise sound and/or tone output that a patient may simply provide to a telephone (e.g., by holding a compliance module near the receiver) such that the information may be automatically transmitted to another device such as a controller.

In some embodiments, the game output provided to the patient may comprise information not directly associated with a typical "game". The game output may comprise, for example, animated representations of an artificial creature and/or an artificial intelligence (e.g., a Tamagotchi™). The occurrence of a patients prescription-compliant events may be necessary, for example, for a patient to maintain the "health" and/or "life" of a displayed and/or rendered cyber-pet. Patients that are compliant and/or substantially compliant, for example, may be presented with game output indicating that their "pet" has grown, learned more skills or words, and/or is otherwise doing well. Non-compliant patients, however, may be presented with game output indicating that the "pet" is hungry, sick, or even dying. According to some embodiments, a "pet" may be shown to suffer maladies and/or symptoms consistent with common problems the patient may suffer if medications or treatment regimes are not followed properly (e.g., as foreshadowing of what may occur if the patient does not improve compliance).

According to some embodiments, the game output provided to the patient may comprise various sounds, pictures, and/or other media (e.g., video) intended to motivate the patient to comply with a prescription. Such media may comprise, according to some embodiments, pictures of friends, family members, or celebrities (and/or other desirable and/or motivational pictures) or sounds and/or voice recordings of friends, family members, or celebrities (and/or other motivational sounds or voice like "Good Job!"). A patient's complaint actions may, for example, cause pictures of grandchildren to be displayed and/or pre-recorded voice tracks from a spouse or other loved-one to be played (e.g., as positive motivation). According to some embodiments, non-compliant events may trigger a direct cellular telephone and/or other communication with a family member and/or health care provider so that the patient may be provided with live support to facilitate and/or encourage compliance.

In some embodiments, the pictures and/or portions thereof may fade and/or disappear in response to non-compliance by a patient. In some embodiments, a picture and/or representation or indication of an available prize (such as a picture of a tropical island representing an available prize trip to Hawaii), for example, may be displayed. According to some embodiments, the displayed prize picture may fade in relation to decreased and/or diminished compliance of a patient (e.g., indicating that the patient's chance of winning the prize is "slipping away").

According to some embodiments, the game output may be provided to stimulate other senses. The game output may comprise, for example, an olfactory indicator such as a pleasing scent. In some embodiments, the olfactory indicator may comprise one or more scents associated with an aromatherapy treatment or may otherwise be configured to facilitate compliance by pleasing or alerting a patient's sense of smell. The scent may, for example, be configured to remind the patient of a pleasing experience and/or to otherwise indicate that the time has come to take a pill or perform a treatment action.

Compliance Module

Figure 3:
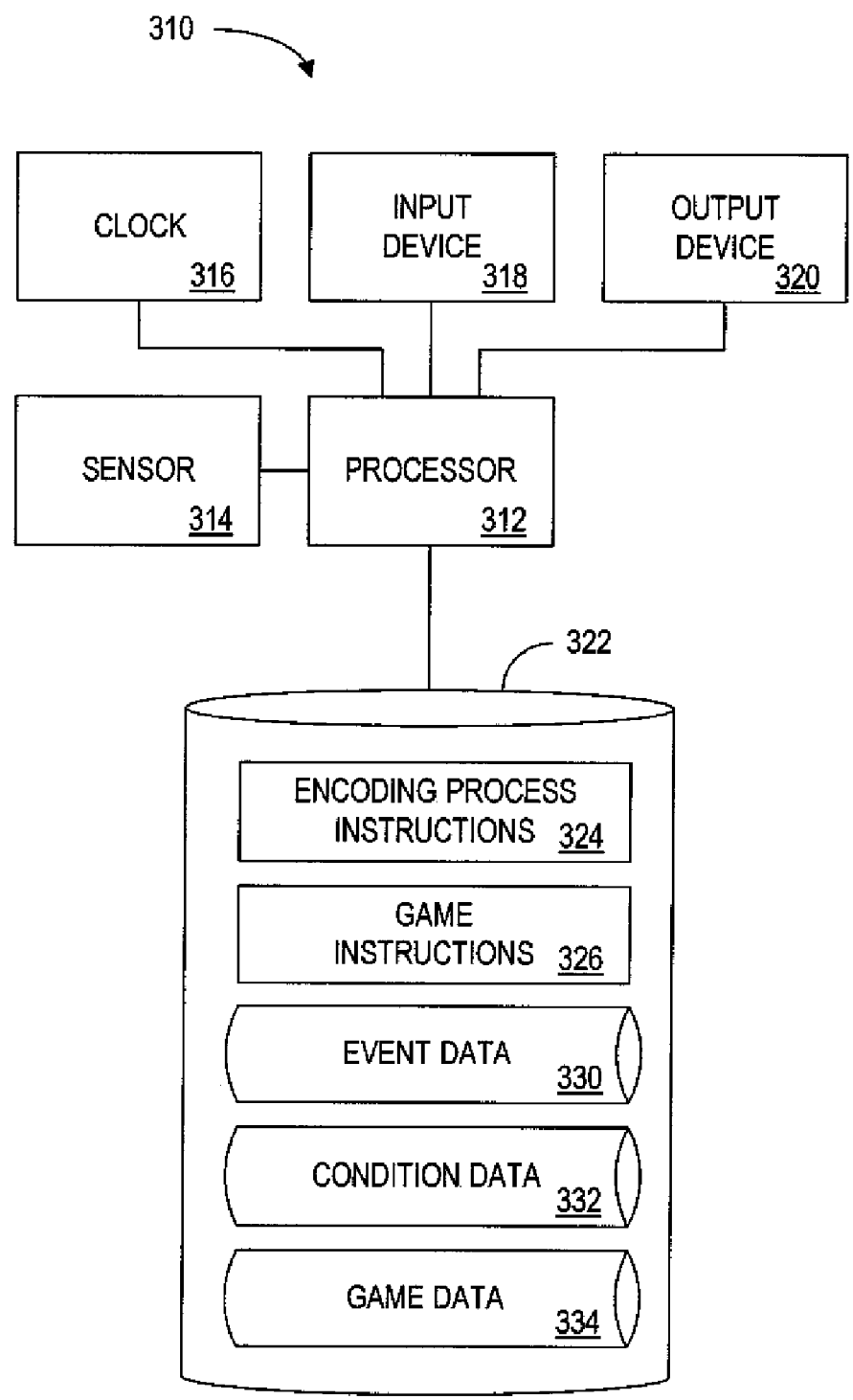
FIG. 3 is a block diagram of a compliance module according to some embodiments.

Turning to FIG. 3, a block diagram of a compliance module 310 according to some embodiments is shown. In some embodiments, the compliance module 310 may be similar in configuration and/or functionality to the compliance module 110 described in conjunction with FIG. 1. The compliance module 310 may, for example, be utilized to monitor and/or record prescription-related events and/or to provide game output to patients to facilitate improved prescription compliance. The compliance module 310 may also or alternatively execute, process, and/or otherwise be associated with the method 200 described in conjunction with FIG. 2. In some embodiments, the compliance module 310 may comprise a processor 312, a sensor 314, a clock 316, an input device 318, an output device 320, and/or a data storage device 322. According to some embodiments, the data storage device 322 may store encoding process instructions 324, game instructions 326, event data 330, condition data 332, and/or game data 334. In some embodiments, fewer or more components, instructions, and/or data than are shown in FIG. 3 may be included in the compliance module 310.

According to some embodiments, the processor 312 may be or include any type, quantity, and/or configuration of processor that is or becomes known. The processor 312 may comprise, for example, an Intel® IXP 2800 network processor or an Intel® XEON™ Processor coupled with an Intel® E7501 chipset. In some embodiments, the processor 312 may comprise multiple interconnected processors, microprocessors, and/or micro-engines. According to some embodiments, the processor 312 (and/or the compliance module 310 and/or other components thereof) may be supplied power via a power supply (not shown) such as a battery, an Alternating Current (AC) source, a Direct Current (DC) source, an AC/DC adapter, solar cells, and/or an inertial generator. A Lithium-ion (Li-ion), Nickel Cadmium (NiCad), and/or Nickel Metal Hydride (NiMH) battery may, for example, supply the necessary voltage and/or amperage to power any or all of the components of the compliance module 310. According to some embodiments, the processor 312 may receive signals from the sensor 314. The sensor 314 may, for example, comprise one or more sensors configured and/or coupled to identify, detect, and/or otherwise determine the occurrence of an event associated with the taking of a substance by a patient.

The sensor 314 may, according to some embodiments, comprise a switch that is coupled to engage in the case that a cap and/or top to a container is opened and/or to disengage in the case that the cap and/or top is closed, latched, and/or otherwise secured. In some embodiments, the sensor 314 may supply the processor 312 with an indication of the number of times that the cap and/or top has been removed and/or replaced. Any type, quantity, and/or configuration of sensor 314 that is operable to identify, detect, and/or otherwise determine the occurrence of a prescription-related event may be utilized. Electrical, electronic, magnetic, and/or mercury switches, pressure sensors, stress sensors, motion sensors, weight sensors, light sensors (including lasers), thermal sensors, acoustic sensors, triggers, gates, switches, barcode or other electronic readers and/or scanners, signal receivers, and/or any other type of sensing device that is or becomes practicable may, for example, comprise the sensor 314.

Examples of sensors 314 may include, but are not limited to, those described in U.S. Pat. No. 4,939,705 to Hamilton, et al. and U.S. Pat. No. 4,616,316 to Hanpeter et al., which are incorporated by reference herein. The type of sensor described by Hanpeter, for example, consists of a blister pack with an array of plastic blisters that define compartments for medication. The backing sheet comprises conductive traces that are respectively ruptured when the medication doses are removed. An electronic memory circuit detects the ruptures and stores the data over a period of time. In some embodiments, other types of sensors 314 may also or alternatively be used. The sensor 314 may, for example, comprise a passive-inductive device, a RF receiver, and/or an RFID reader and/or device. The sensor 314 may, for example, be operable to receive signals from, identify, and/or detect a prescription-related device (such as a medicine bottle or container) and/or may be operable to measure metrics associated therewith (e.g., location identification, position information, mass, weight movement, light transmittance, and/or other information).

According to some embodiments, signals and/or data generated by the sensor 314 may be provided to the processor 312. Such signals and/or data may be indicative of a variety of metrics and/or other information associated with the taking of the substance by a patient. The data may comprise, for example, the number of cap, top, and/or lid removals in a particular time period, a date and time of each of the last twenty (20) removals, durations of removal events, a number of pills dispensed over a given period of time, an amount of a substance removed from a container, movements of a container, etc. Such data may be provided to the processor 312 on a continuous, intermittent, and/or as-need basis. The sensor 314 and the processor 312 need not, for example, be in constant communication.

According to some embodiments, the sensor 314 may transmit the data to the processor 312 a fixed number of times within a given time period. For example, a maximum number of transmitted cap removals and/or other events within a twenty-four (24) hour period might be two. Such a restriction would make it impossible for a patient to generate false cap removal data (e.g., in the case of a pill bottle) by repeatedly opening and closing the cap within a short period of time. A patient with a month long prescription, for example, might realize at the end of the month that he had forgotten to take his medication. Trying to generate a month's worth or cap removal data would be futile since only two cap removal events would be recorded within each twenty four hour period.

In some embodiments, the compliance module 310 may include the clock 316. The clock 316 may, for example, facilitate the compilation, generation, and/or storage of time-related data. According to some embodiments, the clock 316 may maintain an internal (e.g., with respect to the compliance module 310) representation of the time/date and may be used to provide a timestamp that may augment the data provided by the sensor 314. The clock 316 may, for example, be used to track time of day, date, day of week or any other type or configuration of chronographic measurement that is or becomes known. In some embodiments, the clock 316 may provide one or more clock signals to the processor 312 and/or the sensor 314 to synchronize, coordinate, manage, and/or facilitate data transmissions and/or analysis.

According to some embodiments, the clock 316 may be incorporated as part of the processor 312, The clock 316 may, for example, comprise an on-chip or on-die clock circuit incorporated as part of a Central Processing Unit (CPU) that also includes the processor 312. In some embodiments, the clock 316 may comprise an external source that provides time-related data to the compliance module 310 and/or components thereof. The clock 316 may, for example, comprise a device associated with receiving and/or providing standardized time information such as that obtainable from an atomic and/or atomic fountain clock like the National Institute of Standards and Technology-F1 (NIST-F1) cesium fountain atomic clock located in Boulder, Colo., that defines Coordinated Universal Time ("UTC").

In some embodiments, the compliance module 310 may comprise the input device 318. The input device 318 may be or include any type, quantity, and/or configuration of input device that is or becomes known or practicable. The input device 318 may comprise, for example, a keyboard, a keypad, a pointing device (such as a mouse or trackball), one or more buttons or switches, a biometric device, such as a fingerprint or retinal scanner, a magnetic card reader or smart card reader, and/or one or more softkeys and/or variable function input devices. According to some embodiments, the input device 318 may be utilized by a patient to provide information to the compliance module 310. The patient may provide (and/or the compliance module 310 may otherwise receive), for example, input such as a user identifier, a cap, container, and/or "compliance pad" identifier, an insurance policy identifier, and/or a prescription identifier. In some embodiments, the input device 318 may comprise voice recognition capability to allow a patient (and/or other user or entity) to provide verbal information to the compliance module 310. The patient may, for example, speak a code word and/or provide other voice input to the input device 318. The input device 318 may then provide an indication of such input to the processor 312 (e.g., for patient identification and/or other purposes).

In some embodiments, the compliance module 310 may also or alternatively comprise the output device 320. The output device 320 may, for example, be or include any type of output device that is or becomes known or practicable. Examples of output devices 320 may include, but are not limited to, a printer, a speaker, a modem, a Network Interface Card (NIC), a port, a path, a cable, a Cathode Ray Tube (CRT) display device, a Liquid Crystal Display (LCD) device, and/or an LED display device. According to some embodiments, information associated with any of the processor 312, the sensor 314, the clock 316, and/or the input device 318 may be provided, transmitted, and/or displayed via the output device 320. The output device 320 may, for example, comprise a display screen to provide various information to a patient and/or other entity. In some embodiments, the output device 320 may be utilized to provide information processed by the processor 312 and/or information stored via the data storage device 322.

The data storage device 322 may, for example, store the encoding process instructions 324 and/or the game instructions 326 that may be utilized by the processor 312 to provide output information via the output device 318. The data storage device 322 may comprise any appropriate information storage device that is or becomes known or available, including, but not limited to, units and/or combinations of magnetic storage devices (e.g., a hard disk drive), optical storage devices, and/or semiconductor memory devices such as Random Access Memory (RAM) devices, Read Only Memory (ROM) devices, Single Data Rate Random Access Memory (SDR-RAM), Double Data Rate Random Access Memory (DDR-RAM), and/or Programmable Read Only Memory (PROM).

According to some embodiments, the encoding instructions 324 may be operable to cause the processor 312 to encode information. Information received from any of the sensor 314, the clock 316, and/or the input device 318 may, for example, be encoded by the processor 312 in accordance with the encoding instructions 324. Encoding data may provide many advantages. Without knowing how the data is encoded, for example, a patient and/or other entity (e.g., other than a decoding entity) may not be able to (or may not be easily able to) falsify the data. In the case that the data is indicative of prescription-related events and/or game information, for example, encoding may facilitate accurate and secure storage and/or transmission of compliance and/or reward-related information.

The encoding process instructions 324 may comprise, according to some embodiments, one or more encoding and/or encryption protocols to be utilized in encoding data. Examples of various encoding and/or encryption protocols that may be utilized include symmetric key encryption, public key encryption, hash algorithms, digital signatures, and the like. If lower levels of security are required, substitution ciphers or transposition ciphers may be appropriate. Common types of encoding are described in "Applied Cryptography, 2nd Edition" by Bruce Schneier (1996), the encoding and/or encryption descriptions of which are incorporated herein.

In some embodiments, the data encoded by the processor 312 (e.g., utilizing the encoding process instructions 324) may comprise prescription compliance information. The number of cap, top, and/or lid removals in a given time period may, for example, be encoded by the processor 312. According to some embodiments, other data may also or alternatively be encoded. Examples of other data may include user identifiers, cap and/or container identifiers, insurance identifiers, account identifiers, compliance module 110, 310 identifiers, a beginning timestamp and an ending timestamp.

The patient may, for example, enter the number of pills that are taken at each cap removal event, entering the information via the input device 318. In some embodiments, a cap identifier (and/or other information) may be concatenated and/or otherwise combined with the cap removal data. The resulting combined data may then, for example, be encoded by the processor 312. One advantage of such an embodiment is that when the encoded cap removal data is decoded, the identity of the cap (and/or patient, compliance module 310, etc.) may be authenticated in addition to the number of cap removals, preventing a user from providing the encoded cap removal data from another patient's compliance module 310. The encoding process instructions 324 may also provide instructions associated with an integrity test. An indication of a security breach (e.g., tampering) associated with the compliance module 310 (e.g., detected by the sensor 314) may be concatenated and/or otherwise included with the cap removal data prior to the encoding process, for example. Decoding may subsequently reveal evidence of the breach (e.g., and be used to invalidate the compliance results).

In some embodiments, the game instructions 326 may be operable to cause the processor 312 to execute and/or otherwise process data in accordance with one or more games. Upon the detection of an event (e.g., via the sensor 314), for example, the processor may execute the game instructions 326 to provide game-related data to the patient (e.g., via the output device 320). According to some embodiments, the game instructions 326 may include complete code capable of executing, performing, and/or rendering an entire game. In some embodiments, the game instructions 326 may simply comprise instructions associated with game output (e.g., moves, actions, and/or coordinates) and/or game results (e.g., win, loss, and/or other particular outcomes). According to some embodiments, the game instructions 326 may comprise instructions for determining game-related output actions, hints, codes, and/or results based upon prescription and/or prescription compliance events. The game instructions 326 may also or alternatively comprise instructions relating to the control or operation of a separate device.

In some embodiments for example, the game instructions 326 may cause the compliance module 310 and/or the output device 320 thereof to communicate with and/or control another device such as a TV. In the case that a patient is determined to be non-compliant (such as by missing a medication dose), for example, the game instructions 326 may cause the compliance module 310 to send a signal to the TV to turn the TV off, disable video inputs to the TV (such as video game console inputs), or to cause a "V-chip" in the TV to block certain types or instances of programming. In such a manner, for example, patients (particularly children) may be motivated to be compliant with a prescription in order to preserve or obtain TV, movie, and/or video game usage. In some embodiments, compliance events such as taking a pill or medication may be scheduled to be coincident with a particular program, such as a favorite TV program, to further facilitate compliance (e.g., either by simply enhancing remembrance or by blocking the program unless the compliance event occurs).

The data storage device 322 may also or alternatively store the event data 330, the condition data 332, and/or the game data 334. Any or all of these and other types of data may be stored in any number, type, and/or configuration of data storage structures (such as the data storage structures described elsewhere herein) that is or becomes known. The data storage device 322 may, for example, comprise one or more data tables or files, databases, table spaces, registers, and/or other storage structures. In some embodiments, multiple databases and/or storage structures (and/or multiple data storage devices 322) may be utilized to store information associated with the compliance module 310. According to some embodiments, the data storage device 322 may be incorporated into and/or otherwise coupled to the compliance module 310 (e.g., as shown) or may simply be accessible to the compliance module 310 (e.g., externally located and/or situated).

The event data 330 may comprise data associated with events detected, identified, and/or determined by the sensor 314. Events associated with the taking of a substance by a patient, for example, may be detected by the sensor 314 and recorded (e.g., as effectuated by the processor 312) as the event data 330. The event data 330 associated with multiple events (e.g., a months worth of pill bottle openings) may be stored, for example, and then encoded by the processor 312 by executing the encoding process instructions 324. In some embodiments, the condition data 332 may also or alternatively be stored in the data storage device 322. The condition data 332 may comprise, for example, data associated with prescriptions, therapies, and/or other health care regimens. According to some embodiments, the condition data 332 may define one or more conditions and/or time periods associated with such prescriptions. The condition data 332 may be utilized by the processor 312, for example, to determine if detected events are compliant with the prescription conditions. The game instructions 326 may only be executed (and/or may only produce positive results), for example, in the case that an event occurs that is complaint with the condition data 332.

In some embodiments, either or both of the instructions 324, 326 and the data 330, 332, 334 stored in the data storage device 322 may be capable of being updated periodically as is desirable. As new prescriptions, games, and/or other information become available, for example, the data storage device 322 may be updated (e.g., via the input device 318). According to some embodiments, the patient may utilize the compliance module 310 in conjunction with various prescriptions and/or prescription-related devices (e.g., pill bottles). Each time the patient goes back to the pharmacy he may be provided, for example, with a new pill container and new pills. The patient may bring the compliance module 310, in some embodiments, so that data 330, 332, 334 and/or instructions 324, 326 stored in the data storage device 322 may be updated. In this way, revised prescription data may be conveniently entered. The compliance module 310 may also or alternatively be in communication with a server such as the controller 150, so that any updates may be easily and/or automatically executed (e.g., wirelessly and/or remotely).

The game data 334 may comprise any game-related data that is or becomes known or practicable. The game data 334 may, for example, include data indicative of one or more game boards (e.g., bingo boards, battleship boards, minesweeper and/or minesweeper-style boards), card decks (and/or shoes), maps, scratch tickets, and/or other game objects. The game data 334 may also or alternatively include one or more moves, actions, values, results, outcomes, pay tables, probability tables, and/or other metrics associated with one or more games. In some embodiments, the game data 334 may comprise one or more files such as picture, sounds, movie, and/or other audio or video files. According to some embodiments, the game data 334 may be utilized by the processor 312 in executing the game instructions 326. The processor 312 may load one or more lottery and/or bingo numbers from the game data 334, for example, to be provided to a complaint patient via the output device 320. These and other aspects of the various types of stored data according to some embodiments are described in more detail with reference to FIG. 4A, FIG. 4B, and FIG. 4C.

Compliance Module Data Tables

Referring now to FIG. 4A, FIG. 4B, and FIG. 4C, block diagrams of data tables 430, 432, 434 according to some embodiments are shown, respectively. In some embodiments, the data tables 430, 432, 434 may be similar in configuration and/or content to the data 330, 332, 334 and/or data tables described in conjunction with FIG. 3. Any or all of the data tables 430, 432, 434 may, for example, be stored in and/or otherwise associated with the compliance module 110, 310. According to some embodiments, an event data table 430 may store event-related information, a condition data table 432 may store information associated with health care conditions, and/or a game data table 434 may store game-related information, for example. In some embodiments, fewer or more data fields than are shown may be associated with the data tables 430, 432, 434. Only a portion of one or more databases and/or other data stores is necessarily shown in any of FIG. 4A, FIG. 4B, and/or FIG. 4C, for example, and other database fields, columns, structures, orientations, quantities, and/or configurations may be utilized without deviating from the scope of some embodiments. Similarly, the data shown in the various data fields is provided solely for exemplary and illustrative purposes and does not limit the scope of embodiments described herein.

According to some embodiments, such as shown in FIG. 4A for example, the event data table 430 may comprise various data fields such as an "event_id" field 430-1, an "event_type" field 430-2, and/or an "event_time field" 430-3. The "event_id" field 430-1 may, for example, simply store an identifier for each event and/or event occurrence that is recorded in the event data table 430. Each occurrence of an event detected by the sensor 314 may, for example, be represented by a unique identifier such as an alphanumeric code stored in the "event_id" field 430-1. Stored events may also or alternatively be identified and/or described by event types stored in the "event_type" field 430-2. As shown in FIG. 4A, for example, various event types such as "cap_open", "cap_closed", and "patch_applied" may correspond to health care substance (e.g., medication and/or supplement) container openings and closing as well as medicated patch applications, respectively. Many other types of events may also or alternatively be stored and/or identified. Other examples of event types may include, for example, container movements, changes in container weight (e.g., "pill_removed"), emptying or re-filling of a container, and/or use of various medical or health care-related devices (e.g., "inhaler_dosed" or "brace_engaged").

In some embodiments, the time and/or date of every event may be recorded in the "event_time" field 430-3. The clock 316 may be utilized, for example, to determine a specific time (and/or time range or window) in which any given event occurs. Many ancillary time-related metrics may then, according to some embodiments, be calculated based on the stored time stamps. With reference to the exemplary data of the event data table 430, for example, it is recorded (in the first data record) that the cap to a container was opened on the fifth of August at nine eighteen and forty-three seconds in the morning ("08/9/2005 09:18.43") and then (in the second data record) closed on the fifth of August at nine eighteen and fifty-two seconds in the morning ("08/9/2005 09:18.52"). Any processing device (such as the processor 312) may simply calculate that the amount of time that the cap remained open was nine (9) seconds. Such information may be advantageous to determine, for example, if the cap was accidentally opened (e.g., the elapsed time may be determined to be too short for a patient to have removed a pill) and/or if the cap was accidentally left open (e.g., a long period of time elapses before the cap is closed). It may also be advantageous simply to know when a substance and/or regimen was applied. Certain medicines are more effective at certain times of the day, for example, and certain medications and/or therapies may not be effective if repeated too soon or if too much time elapses between doses.

According to some embodiments, such as shown in FIG. 4B for example, the condition data table 432 may comprise various data fields such as a "condition_id" field 432-1, a "condition_type" field 432-2, and/or a "condition_description" field 432-3. The condition data table 432 may store information associated with various conditions relating to prescriptions, therapies, and/or other health care regimens. The "condition_id" field 432-1 may simply store an identifier (such as a unique identifier) for each recorded condition, for example, while the "condition_type" field 432-2 may store a classification and/or grouping associated with the conditions. As shown in FIG. 4A, for example, some conditions may be associated with a "prescription", others may be associated with "dietary" regimens, and/or others may be less-stringent and/or simply "recommended" conditions. Many other classifications may, of course, also or alternatively be practicable. In some embodiments, the "condition_description" field 432-3 may contain a description and/or definition associated with a respective condition.

With reference to the exemplary data stored in the condition data table 432, for example, it is shown that condition "C-0100" (the first data record) defines a condition that a patient must take a pill once a day. In some embodiments, a type, description, and/or identification of the particular pill (or other substance) associated with the condition may also be stored. Such information may also or alternatively be accessible via a linked table such as a "prescription" and/or "medication" table (not shown). The second condition "C-0101" is shown as indicating a "recommended" condition that the pill be taken during a time window between eight and nine in the morning. In some embodiments, such "recommended" and/or secondary conditions may be utilized to provide rewards and/or specific game output to different patients. While any patient satisfying condition "C-0100" by taking a pill once a day may be deemed complaint, for example, those patients satisfying the "recommended" condition "C-0101" may be considered "more" complaint and/or may otherwise be more highly rewarded (e.g., given more lottery numbers, more sweepstakes entries, and/or more bingo numbers or game hints).

According to some embodiments, such as shown in FIG. 4C for example, the game data table 434 may comprise various data fields such as a "game_id" field 434-1, a "game_name" field 434-2, "game_data1" field 434-3, and/or a "game_data2" field 434-4. The game data table 434 may store information associated with various games used to facilitate and/or enhance patient compliance with prescriptions and the related conditions stored in the condition data table 432. The "game_id" field 434-1 may simply store an identifier (such as a unique identifier) for each game, for example, while the "game_name" field 434-2 may store a name of each game. The games shown in FIG. 4C, for example, are "bingo", "lotto", and "minesweeper". Many other games may also or alternatively be stored and/or used as described elsewhere herein.

In some embodiments, the game data fields 434-3, 4344 may store game output (such as the game output determined at 204 in the method 200) and/or other game-related data. As shown, for example, the exemplary records store multiple bingo numbers, lotto numbers, and coordinates, respectively. According to some embodiments, one of these numbers may be provided each time a patient performs a prescription-complaint act. In some embodiments, multiple game output numbers may be provided at any one given time. Accordingly, many game output values may be stored in many more game data fields than are shown in FIG. 4C. In some embodiments, a single game data field may be utilized that links to one or more other fields and/or tables that contain an appropriate amount of game output data. According to some embodiments, the game data fields may simply comprise one or more random number seeds to be utilized by the processor 312 to generate game output (e.g., in accordance with the game instructions 326).

Compliance Games

Figure 5A:
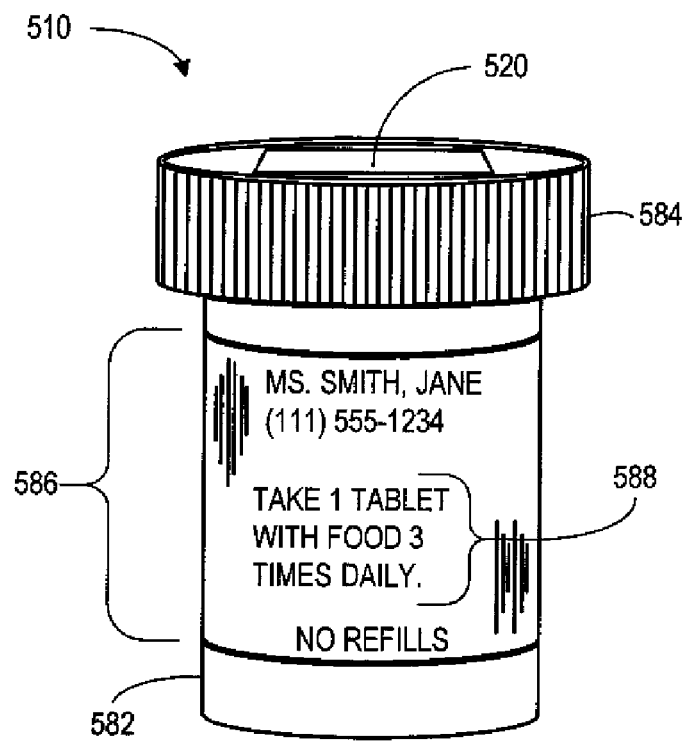
FIG. 5A is a perspective diagram of a compliance module according to some embodiments.
Figure 5B:
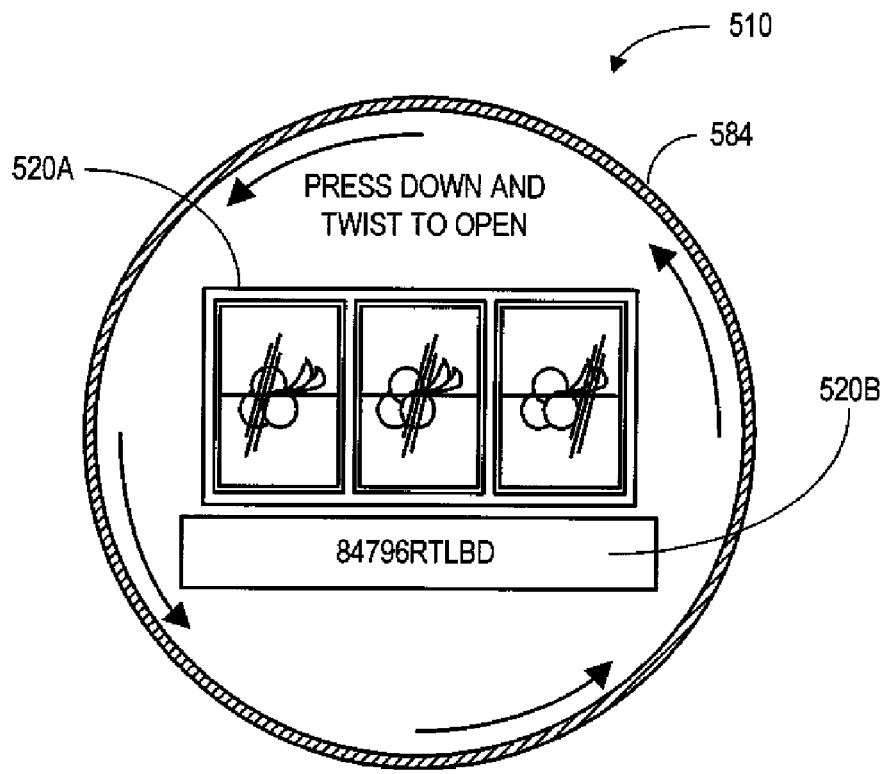
FIG. 5B is a plan view of a compliance module according to some embodiments.

Referring now to FIG. 5A and FIG. 5B, a perspective diagram and a plan view of a compliance module 510 according to some embodiments, are shown respectively. In some embodiments, the compliance module 510 may be similar in configuration and/or functionality to any of the compliance modules 110, 310 described in conjunction with any of FIG. 1 and/or FIG. 3 herein. The compliance module 510 may comprise, for example, one or more output devices 520a-b coupled to a container 582 and/or a cap 584 thereof. The container 582 may, according to some embodiments, be or include any type or configuration of container such as a standard eight, sixteen, thirty, or forty dram (8, 16, 30, or 40-dr) amber clarified polypropylene prescription vial with a childproof, threaded, or snap cap, manufactured by Pharmacy Lite Packaging, Inc. or Pacific Management Holdings (PMH) Manufacturing and Design, LLC, both of Elyria, Ohio. The container 582 may also, of course, comprise any form, shape, size, and/or configuration of container for storing and/or housing health care-related substances or devices that is or becomes known or practicable.

In some embodiments, such as in the case that the container 582 comprises a standard prescription vial (e.g., as shown in FIG. 5A and FIG. 5B), a label 586 may be printed thereon and/or otherwise coupled thereto. The label 586 may, for example, display information such as patient information, pharmacy information, insurance information, and/or condition information 588. According to some embodiments, the condition information 588 may be similar to and/or include the condition data 332. In some embodiments, fewer or more components that are shown in FIG. 5A and/or FIG. 5B may be included in or as part of the compliance module 510.

According to some embodiments, the compliance module 510 may comprise alternate and/or various forms. The standard container 582 shown in FIG. 5A and FIG. 5B, for example, is exemplary in nature and does not limit the scope of the embodiments described herein. In some embodiments, the compliance module 510 may be defined as a particular part or component of and/or may be otherwise associated with the container 582. Instead of the entire container 582 defining the compliance module 510, for example, the container 582 may comprise an entirely standard container with the compliance module 510 incorporated into the cap 584 and/or otherwise coupled thereto and/or associated therewith. It should be understood that the procedures described herein such as the compliance facilitation procedures involving the output of game and/or other information may be performed by and/or associated with any configuration of the compliance module 510 that is or becomes practicable.

According to some embodiments, the compliance module 510 may be utilized to identify, record, and/or otherwise determine whether a patient is compliant with various conditions (such as the condition 588) of a prescription. The compliance module 510 may, for example, identify various events (e.g., at 202) associated with the taking of a substance by the patient. The compliance module 510 may also or alternatively provide game output to the patient (e.g., at 206) to facilitate patient compliance with the prescription.

Applicants have recognized, for example, that many persons enjoy playing games and look forward to the moment at which the result of a game is revealed. For example, many persons enjoy playing games of chance such as slot machine games and greatly enjoy the moment when the reels of the slot machine stop along a payline to reveal the result of the game. Applicants have further recognized that taking medicine (or otherwise complying with a prescription) is typically not an entertaining or enjoyable experience, which is one of the reasons many people either forget or avoid taking their medicine in compliance with the prescription. Accordingly, Applicants have recognized that providing a game interface and/or revealing results of a game (or other game output) in response to the taking of a substance by a patient will be a particularly powerful and effective method for motivating patients to take their medicine and/or otherwise comply with their prescriptions, therapies, or health care regimens.

According to some embodiments, such as shown in FIG. 5A and FIG. 5B for example, the one or more output devices 520a-b of the compliance module 510 may be utilized to output game information such as information associated with the result of a game. In some embodiments, the result of a game may be output via an entertaining game interface, such as the slot machine interface shown in FIG. 5B, provided by the one or more output devices 520a-b. Having the result output via a game interface will further enhance, for example, the patient's enjoyment of obtaining the result of the game. In some embodiments, the label 586 may also or alternatively function as and/or be part of the one or more output devices 520a-b (e.g., the label may be comprised of material operable to output electronic messages, such as a flexible LCD, e-ink™, and/or similar substances or materials). The game interface and/or output may be provided, for example, via the label 586 and/or via more traditional LCD or other output devices 520a-b as shown in FIG. 5A and FIG. 5B.

According to some embodiments, the one or more output devices 520a-b may be included in, for example, (i) the cap 584 of the container 582; (ii) a cavity defined by the container 528 (not explicitly shown); (iii) the label 586 of the container 582; (iv) another portion of the container 582; (v) a peripheral device associated with the container 582 (not shown); or (vi) any combination thereof. The one or more output devices 520a-b may comprise audio or video output devices (such as speakers or transmitters), printing devices, and/or one or more display devices such as an LCD and/or an LED screen. In the case that the one or more output devices 520a-b comprise one or more display devices, for example, information such as still images (e.g., "winner") or animated images (e.g., spinning slot reels) may be shown.

In some embodiments, such as shown in FIG. 5B, the one or more output devices 520a-b may comprise two display screens 520a, 520b. It should be understood, however, that any number, type, or configuration of screens or other output devices 520a-b may be utilized, and that any output may be provided via any available output device 520 and/or any combination of available output devices 520a-b. In some embodiments, the first display screen 520a may provide a representation of a result of a game such as the slot machine interface shown, while the second display screen 520b may provide other output information such as game output, encoded game output, and/or encoded compliance data. The result of a game provided by the first display device 520a may, for example, be represented by a plurality of symbols displayed along a payline, each symbol being displayed on the representation of a respective reel of a simulated slot machine. It should be understood that other interfaces based on other games or types of games may also or alternatively be used. Other games such as poker, solitaire, bingo, minesweeper, battleship, scratch tickets (such as scratch lottery tickets), and/or any other card, board, question, trivia, and/or video games that are or become practicable may be executed by the compliance module 510 and/or provided via the first display device 520a thereof.

In some embodiments, the second display device 520b may display additional and/or other information to the patient. For example, the second display device 520b may display a telephone number for the patient to call, a description of a benefit to be provided to the patient that corresponds to the result of the game displayed via the first display device 520a, a warning (e.g., "take your pill within the next hour in order to remain eligible to win a prize"), and/or a compliance or game-related code that the patient may utilize to obtain rewards (e.g., by providing the code to the controller 150). The patient may call a number provided by the second display device 520b, for example, to provide a code (e.g., also provided by the compliance module 510) to obtain and/or qualify for a reward.

The code may be displayed via the second display device 520b and may, for example, comprise a bingo or lotto number, a game coordinate, and/or other game-related information. Such information may be utilized by the patient, according to some embodiments, to conduct and/or participate in a game. The game may be executed by the compliance module 510 and/or may be associated with external objects and/or devices. The patient may utilize bingo numbers provided by the compliance module 510, for example, to play a bingo card. In some embodiments, the bingo card may be provided electronically via the first display device 520a and/or via an e-ink™ label 586, it may be printed on a standard label 586, engraved or etched on the container 582 and/or the cap 584, and/or may comprise a separate piece of paper or cardstock.

According to some embodiments, such cardstock (and/or label or other card or device) may comprise a latex overlay and/or layer configured to be at least partially scratched-off by a patient. Alternatively, the scratch-off capability may be provided and/or simulated by a touch-screen device such as a flexible LCD display or the like. The card stock and/or game board may comprise, for example, a small, thin, and/or disposable touch-screen device coupled to a processor and a battery (or other power source such as a small photovoltaic device), wherein the device is capable of simulating a scratch-style ticket or card.

In some embodiments, the latex layer, overlay, and/or simulated scratch area may be divided and/or segmented into multiple portions such as may be representative of the various portions of a bingo, minesweeper, minesweeper-type, and/or other game. In some embodiments, the portions may be separated by a margin to reduce the possibility that a patient may accidentally scratch-off an unintended portion. Each such portion may, according to some embodiments, be associated with one or more coordinates, codes, and/or game results. Patients may receive, for example, game output (e.g., for performing compliance-related events) indicative of one or more portions of a game board defined by segmented portions. The patients may then utilize the game output to identify particular portions of the game board to scratch-off. In some embodiments, the latex may be scratched-off to reveal a game result such as a prize or value. According to some embodiments, patients may continue to scratch-off segmented portions until a negative result is revealed (e.g., a mine). In such a manner, for example, patients may decide to continue to seek, upgrade, and/or accumulate winnings and risk voiding the game board (e.g., by revealing a mine and/or other negative result), or may choose to redeem the game board for any currently-revealed prizes.

In some embodiments, the patient may be provided with a chance to win a prize each time the cap 584 is opened or closed in accordance with a condition of a prescription (e.g., condition 588). The compliance module 510 may, for example, comprise a random number generator, a processor (such as the processor 312), a sensor for detecting when the cap 584 is removed and/or replaced (such as the sensor 314), and/or a memory (such as the data storage device 322)—none of which are explicitly shown in FIG. 5A or FIG. 5B. The memory may store, for example, a probability table of available results (e.g., symbol combinations to be displayed via the first display device 520*a* and/or coordinates to be provided via the second display device 520*b*), each result corresponding to at least one random number that may be generated by the random number generator. In some embodiments, the memory may also or alternatively store a payout table of available prizes, each prize corresponding to one or more results that may be displayed via the first or second display devices 520*a-b*.

Thus, for example, every time the sensor determines that the cap 584 is removed (or, alternately, that the cap 584 is replaced), the random number generator may generate a random number. The processor may then, for example, access the probability table to determine the result that corresponds to the random number and cause one of the display devices 520*a-b* to display the result. In the case that the memory also stores a payout table, the processor may further access this payout table to determine the prize corresponding to the result and cause either display device 520*a-b* to display an indication (e.g., a graphical representation or textual description) of the prize. It should be noted that in some embodiments the patient may separately be provided with a list of the prizes available, and the respective result that each prize corresponds to. For example, a patient may be provided with a printed list of prizes and the one or more results corresponding to each prize and/or may be provided with access to a Web site on which this information is posted. In some embodiments, the prizes available to the patient may be customized to the patient and/or may be prizes generally available to all patients participating in a system to facilitate increased prescription compliance.

According to some embodiments, random game results may be generated (either by the compliance module 510 or another computing device) prior to detection of a removal or replacement of the cap 584 (and/or detection of another event) and stored in the memory. In such embodiments, rather than generating a random number in response to a determination that a patient is eligible for a game result, for example, the processor may simply retrieve a game result from memory and output it to the patient. In some embodiments, the processor may retrieve the next available game result that has not previously been output to the patient (such as the game data stored as game data 334 and/or in the game data table 434).

According to some embodiments, the probability of winning a particular prize and/or the prizes available may be dynamic and/or may otherwise change. For example, the longer a patient is compliant with prescription conditions (and/or the more compliant the patient is), the higher the probability of winning a prize may become. In another example, more valuable prizes may be made available to patients of higher and/or longer compliance. For example, the compliance module 510 may store information (e.g., in the memory) identifying the patient and additional information associated with the identify of the patient that may be used to determine the probability to be used in determining a game result for the patient. Such information may include, for example, an indication of the patient's current and/or past compliance with prescription conditions and/or requirements currently and/or previously associated with the patient. In another example, such information may include an indication of the duration for which a condition has been associated with the patient (e.g., if the patient has just begun a prescription, the patient may be provided winning game results more frequently to encourage the patient to become used to taking the medication as prescribed).

In some embodiments, the compliance module 510 may be operable to communicate with another computing device (e.g., the patient's PC). For example, the patient may download software that includes a game interface and that is operable to display game results based on information received from the compliance module 510. For example, the compliance module 510 may transmit a code or other instruction to the PC that causes the software on the PC to provide a game result (e.g., via an output device associated with the PC). The compliance module 510 may transmit such code and/or other instruction via, for example, RF and/or Infrared Radiation (IR) signals, a cable connection between the compliance module 510 and the PC, and/or via the patient, who may be instructed to manually input the information into the PC. In some embodiments, the compliance module 510 may not include a random number generator and/or table of game results in memory or be operable itself to display game results. Instead, the PC and/or other device associated with the patient (e.g., the user device 140) may comprise these elements and be operable to perform these functions in response to input from the compliance module 510. According to some embodiments, both the compliance module 510 and the computing device may be operable to perform these functions and the patient or another entity may select the method via which the game results are to be provided (i.e., via the compliance module 510 and/or via the computing device).

In some embodiments, the patient may be allowed to select one or more game interfaces and/or games via which results are to be displayed. For example, the compliance module 510 may store more than one game and/or game interface in memory. According to some embodiments, different games from a plurality of stored and/or available games may be provided to the patient every time a game result is to be output. Various available games may, for example, be executed in a random order and/or in a round-robin fashion to maintain the interest of the patient. In some embodiments, the compliance module 510 may be operable to determine one or more of the available games that the patient may desire, and these one or more games may be provided to the patient solely or more often than other available games.

In another example, the user may be instructed to visit a Web site that has downloads of various games and/or game interfaces available and may select one of these for download to the memory of the compliance module 510. In yet another example, the patient may be asked (e.g., by a pharmacist) to select a game and/or game interface when the patient takes possession of the compliance module 510 and/or obtains a refill and/or otherwise updates the compliance module 510. This selection information and/or other update information may, for example, be downloaded to the compliance module 510. In yet another example, different compliance modules 510 (such as different container caps 584) may be programmed with different games and/or game interfaces and the patient may be provided with the appropriate device based on the patient's selection of a game and/or game interface. An appropriate device associated with a particular game may also or alternatively be supplied to patients based on demographic and/or other information (e.g., to increase the likelihood that any given patient may find the provided game desirable).

In some embodiments, to further motivate a patient to take their medicine and/or otherwise comply with a prescription, the compliance module 510 may be programmed to initiate a game and/or begin the display of a game result (e.g., via the output devices 520*a-b*) at and/or near the times at which the patient is supposed to take their medicine. Thus, for example, one of the representations of a slot machine reel may display symbols along a payline at a time when the patient is supposed to take the medicine. Additionally (or in lieu of beginning a game or the display of a result of a game), the compliance module 510 may be equipped with an audio output device and may output an audio signal to remind the patient that it is time to take the medicine and/or that the game or display of a game result has been initiated. In some embodiments, the entire game result may be displayed at the time the patient is supposed to take the medicine, yet the patient may only be allowed to claim any prize that is associated with the result if the patient in fact opens and/or re-closes the cap 584 before the full game result is displayed. This may further motivate a patient to take their medicine in compliance with their prescription, since the patient may be reluctant to chance a winning result being displayed and not being able to claim the corresponding prize.

In some embodiments, a result of a game may be displayed for a predetermined length of time (e.g., one hour) at and/or near a time associated with a prescription. For example, if the patient is supposed to take a medication once every twenty-four (24) hours and the last time the cap 584 was opened was yesterday morning at eight (0800), the compliance module 510 may display a result of a game between seven thirty (0730) and eight thirty (0830) in the morning of the current day. If the patient takes the medicine as directed, the patient will be handling the compliance module 510 and/or the container 582 during this one-hour period and will accordingly be provided with the game result. Thus, if the game result is a winning one, the patient will be able to claim the associated prize. If the patient fails to take the medicine as directed, however, the patient will miss seeing the game result displayed during the one-hour period. Many patients will be motivated to remember to take their medicine as prescribed in order to avoid missing any potentially winning game results.

According to some embodiments, rather than being provided with a prize or a chance at a prize upon each opening or re-closing of the cap 584, the patient may instead build and/or accrue equity in a chance at a prize, improving a chance at winning a prize, and/or increasing the value of an available prize with each opening or re-closing of the cap 584 (and/or with each other prescription-compliant action). For example, in one game a patient may win a prize if the patient obtains a predetermined number of occurrences of a particular slot reel symbol over a plurality of game results (e.g., ten cherries). Thus, each time the patient opens or re-closes the cap 584, the patient is hoping to obtain a game result that includes a cherry. The compliance module 510 may be operable to track the number of occurrences of the particular symbol the patient is attempting to collect. In such an embodiment, the frequency of the appearance of the symbol the patient is attempting to collect may change.

For example, the symbol may appear more frequently when the patient first begins to collect the symbol, thus encouraging the patient to comply with a prescription. The probability of "winning" a game may otherwise generally be fixed, manipulated, and/or managed based on actions taken and/or actions that should be taken (e.g., pursuant to a prescription) by the patient. In the case that the game is bingo and the compliance module 510 is provided with access to the layout of a bingo card played by the patient, for example, the compliance module 510 may calculate probabilities based on the layout and bingo numbers already provided to the patient to determine one or more bingo numbers that should currently be provided to the patient. Other games may similarly be analyzed to determine the game output to be provided to the patient. In some embodiments, the game output may be fixed and/or not dependent upon any particular criteria. The compliance module 510 may, for example, be preprogrammed to provide a certain fixed sequence of bingo numbers (and/or other game output) to the patient. In some embodiments, these pre-determined numbers may be pre-associated with a "winning" bingo card, and the patient must simply comply with the prescription to obtain the numbers and realize the "win".

In another example, each time the patient opens or re-closes the cap 584, the patient may be provided with a chance to win a progressive jackpot. In some embodiments, the patient may compete with other patients for the progressive jackpot. Further, each time the patient opens or re-closes the cap 584 a contribution to the progressive jackpot may be made, such that the progressive jackpot increases over time.

In yet another example, a discount or other benefit available to the patient may increase over time as the patient remains compliant, achieves a certain compliance level, and/or is otherwise deemed to be appropriately compliant. For example, a discount in the patient's insurance co-pay, insurance deductible, and/or insurance premiums may increase by a predetermined amount for each predetermined period of time over which the acceptable and/or increased compliance is measured. In such embodiments the patient may be penalized for not complying with a prescription by, for example, a substantial reduction and/or removal of such a discount.

Thus, a patient that has been compliant for an extended length of time and has thus earned a substantial discount will be quite motivated to remain compliant in order to maintain the level of discount that it took so long to earn and/or accrue.

In some embodiments, the patient may be provided with a chance to win a prize each time the patient opens or re-closes the cap 584 and also, in addition, be entered into a bonus game and/or pool for a chance to win a larger prize.

In addition to games of chance, the games playable by the patient may include games of skill and/or games that are part chance and part skill. For example, a question game (such as a "trivia" game) may be made available via the compliance module 510. The questions for the game may be, for example, stored in the memory of the compliance module 510 and/or the memory of another computing device (e.g., the user device 140 and/or the controller 150) with which the compliance module 510 may be operable to communicate.

In one example of a question game, the questions may be related to the substance stored in the container 582 and/or to a prescription associated with the patient. For example, the patient may be asked (and/or otherwise presented with a question) whether the substance causes drowsiness, is to be taken with food, can be taken with alcohol, and/or is compatible with another substance. In such question game embodiments, the compliance module 510 may include an input device (such as the input device 318; not shown in FIG. 5A or FIG. 5B) via which the patient may provide answers to the questions.

In some embodiments, one or more questions may be provided to the patient as a further requirement of claiming a prize. For example, assuming a winning game result has been output to a patient via the compliance module 510, the patient may be required to visit a Web site in order to input an indication of the winning result (e.g., an encrypted code output via the second display device 520*b*) and claim the associated prize. However, before the patient is allowed to claim the prize, the patient may be asked one or more questions. Such questions may, for example, be related to one or more medicines and/or other substances or devices that the patient currently has a prescription, therapy, and/or health care regimen for. In some embodiments, the questions may simply be trivia questions of any practicable and/or desirable nature or complexity.

According to some embodiments, questions may be asked of the patient to allow the patient to remediate previous acts of non-compliance. A patient that misses one or more medication doses, for example, may be able to cure (and/or offset) the defects in compliance by successfully answering one or more questions related to the patient's prescription, likely consequences of missing doses, etc. According to some embodiments, the remedial questions may comprise a test or quiz that the patient must pass (by achieving a certain pre-determined percentage of correct answers) in order to correct partial non-compliance. In some embodiments, the "passing score" required may be determined based on the severity of previous non-compliance. A patient that has only missed a single dose may be required to answer one out of five questions correctly, for example, while a patient that has missed many doses may be required to answer ninety to one hundred percent (90-100%) of questions correctly. In some embodiments, "correction", "remediation", and/or "offset" of non-compliance by answering questions or performing other acts may not "erase" non-compliance (e.g., the statistics of how often the patient took a medication may remain the same), but may preserve or recapture the patient's ability to win a prize or obtain a reward.

In another example of a type of game that may be played via the compliance module 510, the output devices 520*a-b* of the compliance module 510 may output a number or set of numbers that the patient must match to a second number or second set of numbers known to the patient. For example, the patient may win a prize if the number or set of numbers output via the compliance module 510 matches the prescription number of a prescription associated with the patient the patient's social security number, and/or the patient's telephone number. Such a number and/or numbers output via the medicine container may be determined randomly, for example, such as in a manner similar to that described elsewhere herein.

In some embodiments, an input by the patient may be incorporated into the determination of a game result (e.g., for added user enjoyment and further motivation to open the container 582). For example, the exact time at which the patient opens the medicine container may be incorporated into the determination of the random number used to determine the game result. For example, in some embodiments, the random number generator may continuously generate random numbers and the random number generated at the time of the cap 584 removal may be the random number used to produce the game result.

While in some embodiments the game results and/or indications of prizes may be provided to the patient via the compliance module 510 (and/or via another user-associated device), in accordance with some embodiments, the patient may be required to contact another entity and/or device (such as the controller 150) to obtain the game results and/or prize information or for further verification that the patient is in fact entitled to the prize indicated by the game result. This may be the case, for example, for prizes with values over a predetermined value (e.g., prizes worth more than twenty dollars). In some embodiments, the patient may need to provide additional verification and/or validation of having taken the substance as prescribed in order to collect a prize won based on a game result For example, prizes valued above a predetermined threshold may require such additional validation of compliance. According to some embodiments, additional validation of compliance may comprise having the patient provide a code output by the compliance module 510, such as the compliance and/or game codes described in detail elsewhere herein.

In another embodiment, a patient attempting to redeem and/or obtain a large prize may be required to document compliance with a prescription by use of reagent test strips and/or other substance detection devices. For example, a patient may be provided with a plurality of reagent test strips. A test area of each reagent test strip may be impregnated with an appropriate indicator that reacts with a particular substance being tested for. The substance to be taken by the patient may, according to some embodiments, be coated with a quick-dissolving coating containing the substance being tested for. Alternatively, the patient may be provided with a second set of pills and/or other substances coated and/or impregnated with the substance being tested for. A syrup and/or other ingestible and/or edible substance that includes the substance being tested for may, for example, be provided.

In such embodiments, the patient may be required to ingest the second pill and/or other substance each time the prescription-related substance or medicine is taken. When the indicator reacts with the substance being tested for, a color change of the test area of the reagent test strip may occur. In such an embodiment, the patient may be required to place a test strip into his mouth after taking the medicine and store the used test strips in an appropriate container. If and when the patient obtains a game result that corresponds to a prize of at least a predetermined value, the patient may be required to provide one or more of the used test strips as further proof of having taken the required substance. In one embodiment, a reagent test strip may be in the shape of a toothpick.

According to some embodiments, testing for a substance and/or reagent may be accomplished by a toilet and/or other common device outfitted with testing means. A toilet at a testing facility (e.g., at a patient's place of business or insurance agency office) may, for example, comprise physical and/or electronic devices to detect, measure, and/or indicate the presence of a substance. Such devices may be as simple as an integrated test strip or indicator area (presumably a refillable and/or reusable area under the rim or in the bowl of a toilet) and/or may comprise one or more electrodes and a processing device to analyze electrode readings. In some embodiments, the effluent from the toilet may be analyzed by one or more devices coupled to the plumbing leading away from the toilet. Such a device may, for example, be easily retrofitted onto and/or into existing plumbing systems such as those accessible via a basement, crawlspace, and/or utility closet of the patient, employer, insurer, and/or testing facility.

In one or more embodiments the substance being tested for may include a component that degrades or decomposes over time at a predetermined rate, such that a laboratory may be able to determine a length of time since a particular reagent test strip has been used. For example, a laboratory may be able to determine whether the patient used the reagent test strips over time as required or whether all the reagent strips were used at once (e.g., right before sending them into the laboratory).

In yet another embodiment of how a patient may be required to further validate compliance, the patient may be required to visit a physician or laboratory for testing to verify that the patient has been taking the substance. For example, a physician or laboratory may collect a blood sample from the patient for analysis to determine whether the correct dosage of the substance is resident within the patient's bloodstream.

In yet another embodiment of how a patient may be required to further validate compliance, the patient may be provided with pills that each include a bar code imprinted thereon. The patient may, according to some embodiments, also be provided with a bar code scanner (and/or a barcode scanner may be incorporated into the compliance module 510). In such an embodiment, the patient may be required to scan the bar code of each pill before ingesting the pill. If the patient wins a prize (or a prize of at least a predetermined value), the patient may be required to provide the data from the bar code scanner to further verify compliance (e.g., by taking the bar code scanner or memory card of the bar code scanner to a pharmacy).

In some embodiments, friends or relatives of a patient may be allowed to fund one or more prizes available to the patient. For example, as a birthday present, a granddaughter may provide one hundred dollars ($100) to an entity to fund prizes for her grandmother (e.g., a patient). The granddaughter may even be able to specify how the one hundred dollars ($100) is to be provided to her grandmother. For example, the granddaughter may specify that the one hundred dollars ($100) is to be provided as one large prize or distributed over a plurality of small, frequent prizes. The granddaughter may also or alternatively be able to specify conditions upon which the funded prize will or will be likely (e.g., to a certain degree of probability) to be awarded to the grandmother. The granddaughter may specify, fore example, that the grandmother must attain a compliance of at least eighty percent (80%) and/or maintain that level of compliance for one (1) month, in order to qualify for the funded prize. The patient/grandmother may or may not be informed of the source for the funding of the prize. Friends or relatives may also or alternatively be allowed to purchase a chance for the patient to win a relatively large prize. For example, a nephew may pay fifty dollars ($50) to obtain a chance for his aunt (e.g., a patient) to win a one million dollar ($1,000,000) jackpot.

It is understood that some patients may miss a dose of medicine occasionally. In some embodiments, such occasional misses may be allowed so long as the patients admits to (and/or documents) the miss after it occurs and before taking the next dose. The compliance module 510 may, for example, track the indication of the miss and the patient's acknowledgement of the miss before the taking of the next dose. The compliance module 510 may incorporate this information in the next encrypted code and/or game-related output generated for the patient. In some embodiments, the patient may be provided with an opportunity to perform one or more tasks (e.g., taking a test and/or performing additional health-related activities) to make up for missed doses. The compliance module 510 may also or alternatively provide remedial instructions to the patient based at least in part on the missed dosage. It may be appropriate to take one medicine as soon as possible after a missed dose, for example, while it may be appropriate to wait until the next dosage time until taking the next dose of another medicine. Similarly, other missed dosage and/or treatment rules may be associated with taking vitamins, dietary supplements, and/or performing therapies. This information may be provided via either or both of the output devices 520a-b, for example.

It should be noted that various rewards and/or benefits for complying patients are envisioned, including but not limited to: (i) priority servicing (e.g., such that patients needn't wait on hold, wait in a line at a pharmacy, etc.), (ii) information on drug trials (pharmaceutical companies may wish to test drugs with patients who are known to comply with prescriptions, and may pay them for participating), (iii) frequent flyer miles, (iv) prepaid telephone time (e.g., a patient's account is awarded five minutes of phone time for every "success"), (v) premium entertainment content (e.g., access to pay-per-view television, movies, music, and/or Web sites), (vi) health care and/or medical service (e.g., doctors services and/or cosmetic procedures), and/or (vii) cash, discounts, and/or other consideration.

In some embodiments, a benefit for patient compliance may comprise an entry into a sweepstakes or a lottery. For example, a process for providing a benefit to a patient may comprise the following steps: (i) receiving an encrypted code comprising a patient identifier from a patient, (ii) decrypting the code to determine the patients compliance with a prescription, and if the patient is compliant, (iii) entering the patient identifier in a sweepstakes, (iv) drawing a patient identifier at random, and (v) providing a benefit to the patient associated with the drawn patient identifier. In some embodiments, a patient's identifier may be entered into a sweepstakes more than once. For example, a patient may be entered into a sweepstakes once per each "success." In other embodiments, a patient's number of entries may be based on the length of time the patient is compliant, the patient's "success percentage," etc.

Compliance Pad

Figure 6:
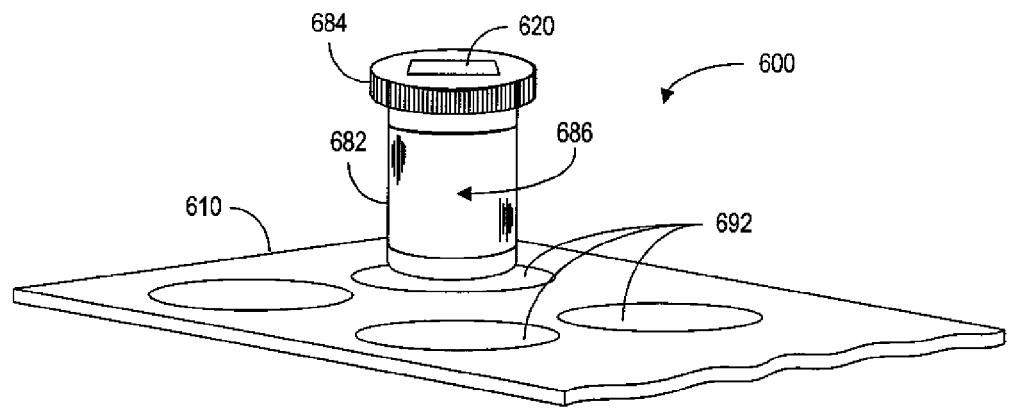
FIG. 6 is a perspective cross-sectional diagram of a system according to some embodiments.

Turning now to FIG. 6, a perspective cross-sectional diagram of a system 600 according to some embodiments is shown. In some embodiments, the system 600 (and/or components thereof may execute, perform, and/or may otherwise be associated with the method 200 described in conjunction with FIG. 2. The system 600 may comprise, for example, the compliance module 610 and/or a container 682. The container 682 may comprise a cap 684 and/or a label 686. In some embodiments, the compliance module 610 may comprise one or more detection areas 692. According to some embodiments, the components 610, 682, 684, 686 of the system 600 may be similar in configuration and/or functionality to the similarly named and/or numbered components described in conjunction with any of FIG. 1, FIG. 3, FIG. 5A, and/or FIG. 5B. The compliance module 610 may, for example, be similar to the compliance modules 110, 310, 510 described elsewhere herein. In some embodiments, fewer or more components than those shown in FIG. 6 may be included in the system 600.

In some embodiments, such as shown in FIG. 6, the compliance module 610 may be or include a pressure-sensitive and/or other pad for facilitating increased patient compliance with prescriptions, therapies, and/or health care regimens. According to some embodiments, such a pressure-sensitive and/or otherwise compliance-facilitating device may be referred to as a "compliance pad" (e.g., a pad-style device that is operable to track and/or enhance patient compliance). One advantage to a compliance pad 610 is that it may be operable to facilitate compliance without requiring substantial and/or any modification to standard medicine and/or other containers 682 (and/or caps 684 thereof. Electronic components may be substantially housed by and/or incorporated in the compliance pad 610, for example, while a substantially standard pill bottle and/or other container 682 may be utilized therewith.

In the case that a patient has many prescriptions and/or must take multiple medications or other substances, for example, the compliance pad 610 may be utilized to easily track compliance with any or all such health care requirements without requiring substantial (or any) modifications to the multiple standard containers 682 used by the patient to store various health-related substances. The detection areas 692 of the compliance pad 610 may comprise one or more pressure-sensitive areas, for example, upon which standard containers 682 may be placed. In some embodiments, the compliance pad 610 may function physically as a container stand (e.g., to stabilize and/or otherwise hold or position the container 682), a coaster, a medicine cabinet and/or medicine shelf or drawer liner (or a shelf itself, and/or may otherwise serve as a location to place one or more health-related substances and/or devices.

In some embodiments, the compliance pad 610 may comprise a weight, mass balance, and/or motion sensor, such that the compliance pad 610 may be operable to (i) determine a first mass of the container 682 (including or not including the cap 684), (ii) detect a first movement and/or removal of the container 682 from the compliance pad 610, (iii) detect a second movement and/or a replacement of the container on the compliance pad 610, (iv) determine a second mass of the container 682, and (v) determine a difference between the first and second masses. In such a manner, for example, the compliance pad 610 may measure compliance by the removal of the container 682 from the compliance pad 610 and determining a change in the mass of the container 682 (e.g., indicating that an amount or quantity of a substance has been removed there from). According to some embodiments, the detection areas 692 may be or include the weight, mass balance, motion, and/or other sensors (such as the sensor 314).

In some embodiments, the detection areas 692 may comprise one or more electrical contacts and/or other sensors operable to determine whether the cap 684 of the container 682 is removed (and/or replaced). The detection areas 692 may, for example, comprise a camera, a photocell, and/or a signal generator and/or receiver. A camera may be pointed substantially vertically, for example, to capture images looking through the bottom of the container 682 toward the cap 684. The images may then, according to some embodiments, analyzed to detect, identify, and/or otherwise determine changes between images that may indicate that the cap 684 is removed, replaced, and/or otherwise manipulated (e.g., twisted or depressed). A photocell may similarly be directed to collect data through the bottom of the container 684 to detect changes in light levels that may indicate events associated with the cap 684. Signals and/or beams such as radar, photo-optic, and/or IR beams may also or alternatively be directed through the bottom of the container 682 toward the cap 684. The reflection, diffraction, and/or other characteristics of such beams may then be analyzed, for example, to determine if the cap 684 is removed, replaced, and/or otherwise manipulated. In some embodiments, such beams may be generated and/or otherwise emanate from the cap 684. The detection areas 692 may then, for example, detect the characteristics and/or presence of such signal and/or beams to determine if the cap 684 is positioned on top of the container 682.

In some embodiments, the detection areas 692 may also or alternatively comprise one or more electrical contacts. The container 682 may also comprise electrical contacts (not shown), for example, that may couple to and/or otherwise engage the contacts of the detection areas 692. The placement of the container 682 upon a detection area 692 may, for example, complete a circuit to indicate that the container 682 has been placed on the compliance pad 610. According to some embodiments, such electrical contacts may also or alternatively indicate whether the cap 684 is coupled to the container 682. An electrical contact of the cap 684 (also not shown) may, for example, couple to an electrical contact near the top of the container 682 to complete a portion of a cap-detection circuit. This cap-detection circuit may in turn be coupled via an electrical trace to a contact near the bottom of the container 682 that may engage and/or communicate with the detection areas 692 to indicate (i) the presence of the container 682, and/or (ii) the coupling and/or presence of the cap 684. In some embodiments, any or all of these electrical contacts and/or traces may be incorporated into the compliance pad 610, the container 682, and/or the cap 684, and/or may be coupled thereto via any techniques that are or become known or practicable. Electrical traces of the container 682 may, for example, be incorporated into the label 686, such that a substantially standard container 682 may be easily modified to provide electrical indications to the detection areas 692.

According to some embodiments, communication between the container 682, the cap 684, and/or the detection areas 692 may be partially and/or entirely wireless. Passive induction devices may be utilized, for example, to allow the detection areas 692 to detect the presence and/or proximity of the container 682 and/or the cap 684. In some embodiments, RFID devices may also or alternatively be utilized. Each container 682 and/or cap 684 may be equipped with an RFID tag, for example, that is capable of being either actively or passively detected by the detection areas 692. Such an RFID tag may indicate various information such as a unique identifier, container 682 and/or cap 684 data, and/or prescription or substance information (e.g., type of substance and/or medication, expiration date, prescription rules, and/or compatibilities with other medications).

Such unique identification information may, according to some embodiments, be utilized by the compliance pad 610 to determine and/or indicate potential incompatibility of substances. In the case that a patient taking multiple medications places two containers 682 on and/or near the compliance pad 610, for example, the detection areas 692 may determine (e.g., via RFID technology) the nature and/or identification of the medicines that are present. A compatibility table, matrix, and/or other file or data may then be accessed, for example, to determine if the two medications may be safely taken together. In the case that a conflict is determined, the compliance pad 610 may alert the patient and/or another entity of the potential danger. In the case that prescription information is obtained from the container 682, the compliance pad 610 may also or alternatively provide prescription-specific information to the patient (such as "take one pill with food daily", "avoid sunlight", etc.).

Figure 7:
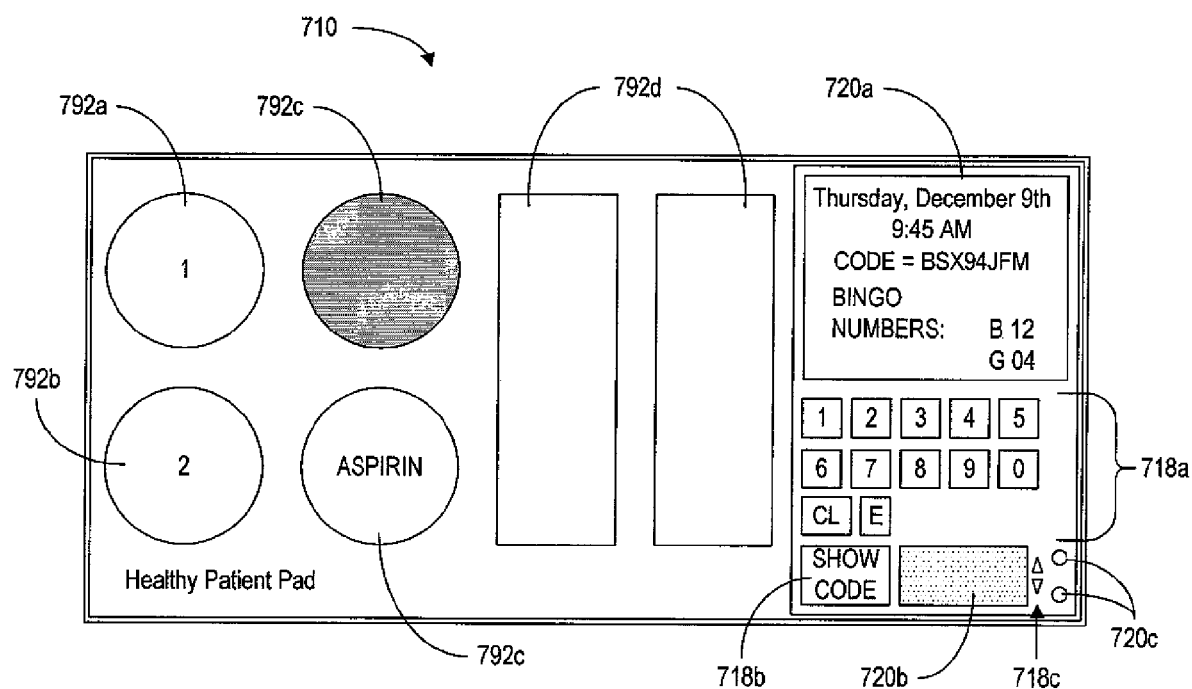
FIG. 7 is a plan view of a compliance module according to some embodiments.

Turning now to FIG. 7, a plan view of a compliance module 710 according to some embodiments is shown In some embodiments, the compliance module 710 (and/or components thereof may execute, perform, and/or may otherwise be associated with the method 200 described in conjunction with FIG. 2. The compliance module 710 may comprise, for example, one or more input devices 718*a-c*, one or more output devices 720*a-c*, and/or one or more detection areas 792*a-e*. The input devices 718*a-c* may comprise a keypad 718*a*, a command button 718*b*, and/or directional controls 718*c*. The output devices 720*a-c* may comprise a display screen 720*a*, a speaker 720*b*, and/or one or more LED devices 720*c*. According to some embodiments, the components 718*a-c*, 720*a-c*, 792*a-e* of the compliance module 710 may be similar in configuration and/or functionality to the similarly named and/or numbered components described in conjunction with any of FIG. 3, FIG. 5A, FIG. 5B, and/or FIG. 6. In some embodiments, fewer or more components than those shown in FIG. 7 may be included in the compliance module 710.

In some embodiments, the compliance module 710 may be similar in configuration and/or functionality to the compliance module 610 described in conjunction with FIG. 6. As shown in FIG. 7, for example, the compliance module 710 may be configured as a "compliance pad". The compliance pad 710 may, according to some embodiments, be provided to a patient by an employer, a health care provider, and/or an insurance entity. The compliance pad 710 may, for example, be associated with one or more health benefit, discount, and/or study programs associated with offered by a health insurance carrier. Applicants have realized, for example, that wellness programs such as the Healthy Rewards® program offered by CIGNA® may be advantageously supplemented via utilization of the compliance pad 710.

Such programs typically incorporate three (3) elements in an attempt to preemptively reduce health care costs. Patients are given incentives, for example, to (i) exercise, (ii) obtain regular physical examinations, and (iii) follow basic nutritional guidelines. The widespread and extremely expensive occurrence of non-compliance with prescriptions, therapies, and/or other health care regimens, however, has continued to prove difficult to address. Utilization of the compliance pad 710 and/or execution of the various procedures and/or other embodiments described herein, however, may prove to be an effective fourth element of wellness programs that may function to more effectively reduce health care costs and associated health care premiums (e.g., for individuals and companies alike).

For example, the compliance pad 710 may be or include a pad-like device that is provided to insured patients as part of a wellness program. The compliance pad 710 may be configured, according to some embodiments, to monitor patient compliance with a prescription and/or to provide game-related output to entice the patient to increase compliance. In some embodiments, the compliance pad 710 may be comprised of one or more flexible mediums such as a flexible Printed Circuit Board (PCB), a flexible LCD, rubber, plastic, and/or other flexible and/or semi-flexible materials. According to some embodiments, the compliance pad 710 (and/or a portion thereof may be comprised of foam, visco-elastic foam, glass, aluminum, steel, and/or a fabric such as polyester. The compliance pad 710 may, for example, be similar in composition and/or flexibility to a mouse pad. One advantage to a flexible compliance pad 710 may be that it is more easily transported (e.g., it may be rolled-up and/or folded) and/or more easily maintained (e.g., less subject to breakage or damage) than a rigid device. Any configuration of materials, shapes, sizes, and/or flexibilities that are or become desirable may, however, be utilized to define the compliance pad 710.

In some embodiments, the compliance pad 710 may comprise the one or more input devices 718*a-c*. The compliance pad 710 may comprise, for example, the keypad 718*a*, the command button 718*b*, and/or the directional controls 718*c*. The keypad 718*a* may, according to some embodiments, comprise a standard layout of keys such as that utilized on most telephones and/or calculators. In some embodiments, the keypad 718*a* may be utilized by a patient to enter information into the compliance pad 710. The patient may, for example, be able to configure preferences (e.g., contrast, colors, font, and/or modes) and/or customize the display screen 720*a*, enter information (e.g., prescription information, insurance information, and/or patient identification information), provide access codes such as a Personal Identification Number (PIN), and/or otherwise interact or interface with the compliance module 710. In the case that games and/or game interfaces are presented via the display screen 720*a*, for example, the patient may be able to utilize the keypad 718*a* to provide game input (e.g., moves, commands, and/or other actions) to the compliance module 710. In other words, the patient may utilize the keypad 718*a* to "play" a game via the compliance pad 710.

According to some embodiments, the command button 718*b* may also or alternatively be utilized to provide input to the compliance pad 710. As shown in FIG. 7, for example, the "show code" command button 718*b* may be utilized by the patient to command the compliance pad 710 to show a code (e.g., via the display screen 720*a*). The patient may utilize the command button 718*b*, for example, to cause the compliance pad 710 to display a compliance and/or game-related code such as those codes described elsewhere herein. At the end of a compliance period, for example, the patient may press the command button 718*b* to obtain a code that may be called-in to a health care entity to determine compliance, participate in a game, and/or to qualify for and/or receive prizes or other rewards. Other functionalities of the command button 718*b* may, of course, also or alternatively be implemented. The command button 718*b* may be utilized, for example, to obtain a compliance status (e.g., "complaint" or "non-compliant", or "70%") and/or a game status (e.g., "win!" or "sorry"). In some embodiments, the command button 718*b* may not be included in the compliance pad 710 and/or may be incorporated into the keypad 718*a*.

In some embodiments, the directional controls 718*c* may also or alternatively be included in the compliance pad 710. The directional controls 718*c* may, for example, be utilized to provide direction-related input to the compliance pad 710. As shown in FIG. 7, for example, the directional controls 718*c* may be utilized to increase or decrease the volume of the speaker 720*b*. Other such input may also or alternatively be provided by the directional controls 718*c*. The directional controls 718*c* may, for example, be utilized to provide directional input to play a game via the compliance pad 710 and/or to navigate menus provided via the display device 720a. Although only two directional controls 718c are shown in FIG. 7, it should be understood that fewer (e.g., a single multi-directional pad-style button) or more (e.g., a four-way grouping of controls) directional controls 718c may be included in the compliance pad 710.

The output devices 720a-c may be utilized to provide any of various types of output to the patient (and/or other entities). The display device 720a may, as shown in FIG. 7 for example, provide indications of the time and date, a code, and/or game-related information (e.g., bingo numbers). The code may comprise an encoded and/or encrypted compliance code indicative of the patient's compliance with a prescription, for example, while the game-related information may allow the patient to participate in a game (e.g., to entice the patient to interact with the compliance pad 710). Any other types of information that are or become practicable may also or alternatively be provided via the display screen 720a. The display screen 720a may, for example, be utilized to provide a game interface such as a slot machine, video game, and/or trivia game interface.

According to some embodiments, the speaker 720b may also or alternatively be utilized to provide information to the patient (and/or another entity such as a pharmacist). The speaker 720b may, for example, provide audible and/or spoken commands and/or alerts to the patient, such as "time to take medicine", "warning—incompatible medicines!", "game time!", "please call-in the code", and/or "you have won!". The speaker 720b may, according to some embodiments, be utilized in conjunction with the display device 720a. In the case that the display device 720a provides and/or renders a game or game interface, for example, the speaker 720b may provide coordinated and/or attendant sounds and/or other audible game output. In some embodiments, the volume of the speaker 720b may be controlled via the directional controls 718c.

The compliance pad 710 may also or alternatively comprise the LED devices 720c. The LED devices 720c may, for example, be utilized to provide visual indications to a patient and/or other entity. A green LED device 720c may indicate current compliance, for example, and/or a red LED device 720c may indicate non-compliance and/or an error (e.g., low battery). A combination of different colored LED devices 720c (such as shown in FIG. 7) may be utilized to provide many and/or more complex signals and/or output. The LED devices 720c may be blinked and/or pulsed at various rates, in succession, in alternating succession, and/or may otherwise be activated, for example, to indicate any of a variety of practicable information. According to some embodiments, one or more LED devices 720c may be provided for each detection area 792a-e. A green LED device 720c adjacent to a detection area 792a-e may indicate, for example, that a container is currently detected by the compliance pad 710 (e.g., via that particular detection area 792a-e), while a red LED device 720c and/or an inactive LED device 720c may indicate that no container is currently detected via the detection area 792a-e.

In some embodiments, the detection areas 792a-e may be similar in configuration and/or functionality to the detection areas 692 described in conjunction with FIG. 6. The detection areas 792a-e may, for example, comprise pressure-sensitive areas of the compliance pad 710. Any or all of the detection areas 792a-e may, according to some embodiments, comprise any type or configuration of sensor and/or detector that is or becomes known or available. In some embodiments, substantially an entire surface (such as the upper surface) of the compliance pad 710 may be pressure-sensitive. The detection areas 792a-e may accordingly be designated areas of the pressure-sensitive compliance pad 710. The keypad 718a and/or other input devices 718a-c may also or alternatively be incorporated as designated areas upon such as pressure-sensitive compliance pad 710. According to some embodiments, the detection areas 792a-e may comprise one or more undesignated and/or unassigned areas. The surface of the compliance pad 710 may be substantially unmarked and/or unassigned, for example, and a patient may simply place containers anywhere upon the surface to activate a single detection area 792. In some embodiments, such as shown in FIG. 7, multiple distinctly designated and/or marked detection areas 792a-e may be provided.

The detection areas 792a-e may be utilized to detect, track, weigh, and/or otherwise monitor or manage containers placed thereon. Some detection areas 792a-d may be configured and/or marked to monitor pill bottles and/or liquid vials, for example, while other detection areas 792e may be configured to monitor pill boxes, food containers, and/or other rectangular objects. Other configurations of detection areas 792a-e may also or alternatively be utilized. An "open" detection area with no distinct internal boundaries (such as described above) and/or other areas designed to accommodate bags and/or particular types of medical devices may also or alternatively be utilized, for example.

In some embodiments, the detection areas 792a-d may be configured to provide output. In the case that multiple prescriptions and/or containers are to be monitored by the compliance pad 710, for example, it may be desirable to be able to separately and/or distinctly identify where each such container should be placed. The first and second detection areas 792a-b are shown as being numbered, for example, to facilitate patient placement and/or organization of containers. Such numbers may be printed on the surface of the compliance pad 710, for example, and/or may be displayed dynamically via embedded LCD and/or LED devices. As shown with respect to the third detection area 792c, color-coding may also or alternatively be utilized. The patient may be provided with prescription vials of various colors and/or with various colored labels, for example, and the detection area 792c may be color-coded to correspond to one or more of the particular containers. Such color-coding may be printed directly on the compliance pad 710 and/or may be indicated by one or more lights such as color LED or LCD devices. In some embodiments, a name and/or other identifier of a particular medicine may be displayed. As shown with respect to the fourth detection area 792d, for example, the name "aspirin" may be displayed to indicate that an 'aspirin' container should be placed on the fourth detection area 792d.

According to some embodiments, the output-configured detection areas 792a-d may also or alternatively be utilized to provide game-related functionality. Games such as "Simon says" and/or other color, pattern, and/or repetition games may be played via variably colored touch-sensitive detection areas 792a-e, for example. In some embodiments, the patient may be prompted to re-arrange various containers as indicated by the detection areas 792a-e and/or may otherwise be prompted to undertake actions of skill or timing as part of a game. In the case that prizes or rewards are available for obtaining successful game results, such games may greatly increase the interest in taking medication and participating in the attendant games provided by the compliance pad 710.

Controller Method

Figure 8:
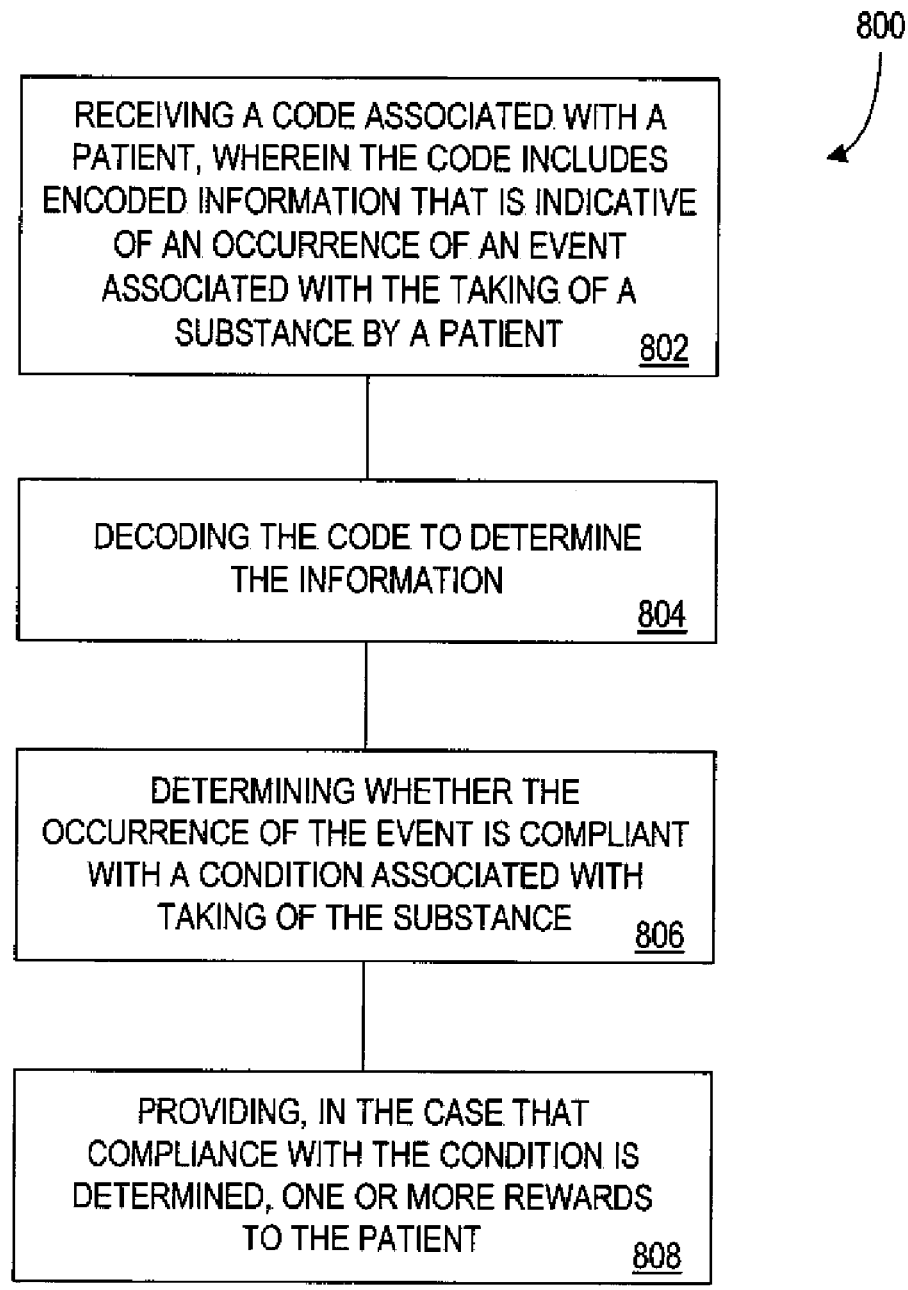
FIG. 8 is a flow diagram of a method according to some embodiments.

Referring now to FIG. 8, a flow diagram of a method 800 according to some embodiments is shown. In some embodiments, the method 800 may be performed and/or implemented by and/or otherwise associated with the controller 150 described in conjunction with FIG. 1. According to some embodiments, the method 800 may begin at 802 by receiving a code associated with a patient, wherein the code includes encoded information that is indicative of an occurrence of an event associated with the taking of a substance by a patient. According to some embodiments, the code and/or information may be recorded on a smart card and/or other storage medium and physically delivered to an entity for processing. In some embodiments, a patient may receive such a code from a compliance device such as the compliance modules 110, 310, 510, 610, 710 described herein, and may call a number associated with a health care provider and/or insurer of the patient. The compliance module and/or pad may, for example, be provided to the patient by a health care provider, employer, insurance provider, and/or other entity (such as an entity that operates the controller and/or performs the method 800).

The patient may then, for example, provide a verbal and/or other indication of the code (e.g., input via a telephone keypad) to a controller and/or other receiving device or entity. In some embodiments, an Interactive Voice Response Unit (IVRU) associated with an insurance carrier and/or a third-party may, for example, receive the code from the patient. The code may include information indicative of prescription-related statistics associated with the patient (e.g., a number of cap removals, amount of substance taken, or other patient actions) and/or may include an indication of a status and/or determination of compliance (e.g., such as in the case that a data compliance module is provided with prescription-related conditions). The code and/or information may also comprise time stamps, patient, compliance module, and/or account identifiers, tamper flags, and/or other such information. According to some embodiments, the code may also or alternatively comprise information indicative of game output and/or results.

The code and/or encoded information may, for example, indicate that the patient has won a game (e.g., associated with a compliance module). The patient may be provided with a game board such as a Monopoly®, battleship, minesweeper, bingo, card game, and/or other game board, for example, and the code and/or encoded information may be indicative of a result and/or action associated with the game. In some embodiments, such as in the case that the received information indicates that the patient is the winner of a game, the patient may be awarded and/or provided with a prize. According to some embodiments, the code itself may indicate a particular prize that the patient has won (and/or earned by being compliant).

According to some embodiments, the patient and/or compliance module may be actively solicited for the code. From the patient's perspective in other words, the utilization and/or application of the information generated by a compliance module may be a substantially passive process (e.g., requiring little or no input or intervention on the part of the patient). The controller may, for example, initiate a communication session with the patient such as by placing a phone call and/or sending an e-mail. This may occur, for example, at the end of a pre-designated compliance period, such as at the beginning or end of every month. An automated voice system may, in some embodiments, prompt the patient for the code. An operator and/or other device or entity may also or alternatively request the code from the patient and/or from the compliance module. A response to the query may then be received. The patient may enter the code via a touchtone telephone keypad, for example and/or speak the code into the telephone receiver.

In some embodiments, the method 800 may continue by decoding the code to determine the information, at 804. Various decoding and/or decrypting algorithms may be used, for example, to determine the encoded information based upon the received code. In some embodiments, different decoding and/or decrypting algorithms may be utilized for codes received from different patients and/or different compliance modules. According to some embodiments, other information may be received (e.g., at 804) in addition to the code itself. A public key and/or other decoding, identification, or routing information may, for example, be received and utilized to facilitate decoding or other processing of the code.

In some embodiments, the controller may retrieve decoding process instructions from a data storage device and then execute these instructions to decode the received data in order to derive one or more parameters indicative of the decoded data. According to some embodiments, such as in the case that the data is encoded by calculating a hash value associated with the data, the controller may execute the decoding process instructions to apply the same hash algorithm to the data to determine the associated hash value. If the two hash values are the same, the data may, for example, be authenticated. In some embodiments, the controller may additionally determine whether a positive tamper indication is present. Although this determination may be effected in a number of conventional ways, in the some embodiments, the determination may be made based on a tamper flag decoded from the received information. In the case that the controller determines that tampering is evident, the controller may store an indication of such tampering in a database such as the data tables described elsewhere herein.

According to some embodiments, the result of decoding may be provided to the patient, providing immediate feedback as to the receipt, content, and/or effect of the compliance and/or game data. This output may be provided, for example, in audio form via an IVRU and/or operator or via other electronic means (e.g., e-mail). The controller may additionally update stored patient data based on the decoded information. For example, a patient record may be flagged to indicate that the patient has tampered with a compliance module and/or that data associated with the patient has been received.

It should be noted that a code may be not be encrypted, but scrambled in some other manner (e.g., the sum of all the digits of the code is determined to be less than ten, and the code is therefore valid). According to some embodiments, a code may be expressed as and/or converted to a non-human-readable form (e.g., a three-dimensional barcode) without requiring any other form of disguise and/or encryption. In some embodiments, codes may not be encrypted, scrambled, encoded and/or otherwise secured at all. A code may, for example, simply correlate to a result stored by the controller that other entities (such as the patient) may be unable to find meaning in without access to the stored cross-reference table.

In some embodiments, the method 800 may continue at 806 by determining whether the occurrence of the event is compliant with a condition associated with the taking of the substance. The controller 150 may, for example, analyze the decoded information to determine a compliance associated with a patient. In some embodiments, the actual compliance may already have been calculated and/or determined (e.g., by a compliance module) and the controller may simply need to identify such results within the decoded information. According to some embodiments, such as in the case that the information contains indications of actions taken by a patient, the actions may be compared to various prescription conditions to determine levels of compliance. In some embodiments, receipt of appropriately coded information may itself be deemed a "compliant" event such as in the sense that by simply allowing the controller to monitor the patients actions, the patient has been complaint.

According to some embodiments, the patient (and/or another entity) may be provided with a compliance report. Upon determining patient compliance and/or upon the expiration of a pre-determined compliance time period, for example, a report may be generated to indicate (i) current compliance status, (ii) compliance history (e.g., during the compliance period and/or compared to previous compliance periods), (iii) compliance goals, (iv) suggestions for improving compliance, (v) rewards and/or prizes won or available (e.g., due to achieved compliance), (vi) encouragement messages from family and/or friends, (vii) competition information (e.g., ranks and/or standings of a patient and all other members of a certain group), and/or (viii) other compliance or patient-related information. Such a report may be very advantageous in analyzing a patient's compliance. The patient, the patient's health care provider (e.g., doctor or nurse), the patient's insurer, and/or a third-party analysis entity may, for example, utilize the compliance report to manage and/or increase compliance, distribute benefits or rewards, and/or study or analyze health care statistics.

The method 800 may continue at 808, for example, by providing, in the case that compliance with the condition is determined, one or more rewards to the patient. The patient may be provided, for example, with one or more benefits based on a number of recorded successes (e.g., instances of compliant events), a percentage of recorded successes, and/or a ratio of recorded successes to recorded failures (e.g., a compliance percentage). The code received by the patient from the compliance module (and decoded and/or processed by the method 800) may, according to some embodiments, be used to redeem one or more benefits. For example, a patient acquiring one hundred (100) consecutive successes may be provided with a code that may be entered into a Web site to achieve a discount on goods or services offered by the Web site. According to some embodiments, the rewards may comprise one or more trophies, plaques, certificates, badges, medals, and/or other insignia and/or indications of achievement (e.g., a hat or shirt that says "Happy Valley Nursing Home's Best Pill-taker!" or a plaque that shows "Jogger of the Month: April, 2005").

In another example, a patient may be provided with a code entitling the patient to a number of entries in a sweepstakes. For example, for every five successes, the patient may be provided with an encrypted code, which the patient may "call in" to a sweepstakes telephone service controller. Alternately, at the end of every month, a patient may be provided with a number of benefits (e.g., sweepstakes entries and/or lottery tickets or numbers) based on a compliance percentage (e.g., the number of successes divided by the number of elapsed time periods). In one embodiment, the value of a benefit (e.g., discount amount, or sweepstakes jackpot) may increase relative to the number of a patient's successes.

According to some embodiments, the reward given to a patient may be determined based at least in part on the compliance of other patients. Patients may compete, for example, to obtain higher compliance ratings, with the most-compliant patient and/or patients receiving a reward or prize. Groups of patients may also or alternatively compete together to obtain rewards. Nursing home and/or other groups of patients may attempt to achieve group compliance goals, for example, to obtain a reward for the nursing home and/or for another associated third-party such as a charity. According to some embodiments, compliance results may be available to competing patients such that patients may be more likely to view the current standings and attempt to achieve higher compliance to outperform other patients and receive rewards. Such compliance "races" may be quite useful in giving patients a competitive reason to increase prescription compliance.

In one or more embodiments, a benefit may comprise a set of lottery numbers. For example, so long as a patient is compliant, the patient may be provided with several numbers every week for a state-drawn lottery. The numbers may be output, for example, via an output device associated with the compliance module. In one example, an LED screen may depict five lottery numbers, as well as the date/time of the drawing and an encrypted code, which represents the date and the lottery numbers displayed to the patient. Should the numbers be winners, the patient may provide the encrypted code to a lottery agent so that the claim to winnings may be validated. In another example, a medicine container may further comprise or be associated with a printer that may function to print a physical lottery ticket.

In one or more embodiments, the patient may be allowed to select their own lottery numbers for a drawing. For example, in one embodiment the compliance module may output a code whenever the patient is eligible for an entry into a lottery drawing. The patient may use the code to access a Web site, via which the patient may select a set of lottery numbers. The Web site may first decrypt the code (e.g., at 804) to verify that the patient is in fact eligible to select the set of lottery numbers. In another example, a patient may provide a set of preferred lottery numbers to the compliance module and/or to another entity (e.g., a pharmacist may download the selected numbers to the compliance module or the patient may register, with the controller, the selected set of numbers as associated with the patient via a Web site or other connection). In this latter example, whenever the patient is eligible to be entered into a lottery drawing, the patient may be provided with a code. The patient may then call in this code to the controller and/or input the code into a Web site in order to have the preferred set of lottery numbers automatically entered into the next available lottery drawing. Alternatively, the compliance module may be operable (e.g., via a modem) to communicate with the controller whenever the patient becomes eligible for an entry into a lottery drawing, in order to transmit to the controller an indication of the patient's eligibility. Upon receiving such an indication, the controller may automatically enter the patient's preferred set of lottery numbers into the next available lottery drawing.

In or more embodiments, a compliance module may comprise a random number generator. In one such embodiment each cap removal and/or other prescription-related event might trigger the generation of a random number. A benefit may then be awarded based on a result associated with the random number (e.g., "You've won a Ford® Explorer™? Call 1-800-555-5555 and enter code 205034059"). In one embodiment, the random number itself may be displayed to the patient. The patient may then determine the result associated with the random number by calling an entity such as the controller 150 with the random number and/or by visiting a Web site that displays the results associated with various random numbers. In another embodiment, the result associated with the random number may be displayed via an output device associated with the compliance module.

The data table comprising a list of random numbers and their corresponding results may be stored in a memory of the compliance module and/or another processor responsive to instructions from the compliance module. For example, the data table may be stored in the memory of a computing device (e.g., the user device 140 onto which appropriate software including the table has been loaded) and the compliance module may include an IR and/or RF-based output device via which the computing device may be instructed to access the table and display the result associated with the random number. In another example, the patient may manually enter the random number into a computing device (e.g., the patient's PC or PDA onto which appropriate software including the table has been loaded), thus causing the computing device to display the result to the patient.

It should be noted that a "result" may comprise a representation or indication of a benefit to be provided to the patient. For example, a result may comprise a slot machine like collection of graphical symbols (e.g., cherry-cherry-cherry). A data table may store a plurality of available results and the benefit (if any) associated with each respective result. This data table may be stored, for example, within a memory of the compliance module, within the memory of another computing device (e.g., the user device 140 onto which appropriate software including the table has been loaded), and/or the memory of the controller 150.

In some embodiments, historical patient data may provide the basis for rewards or penalties, and could serve as a basis for making pricing decisions for future insurance coverage. Patients might be provided with higher reimbursement levels for drugs for which they had complied with the prescription instructions. For example, a patient might pay one hundred ($100) for a prescription, with the insurance provider reimbursing one quarter (¼) of that amount if the patient does not comply with the prescription requirements, and one half (½) of that amount if the patient does comply with the requirements. Insurance companies might also require that the patient call in with encoded data before any reimbursements are provided.

It should also be recognized that a compliance module may include processing instructions to store compliance statistics associated with a patient, and may output an encoded code only upon reaching a predetermined reward threshold. Thus, encoding process instructions could include code that outputs encoded data only when the patient opens an associated pill or other container a number of times equal to the number of doses stored within the container.

In some embodiments, a pharmaceutical supplier may offer rebates to purchasers of pharmaceuticals based on compliance and/or usage (e.g., as indicated by the encoded information). A physician may also or alternatively provide a money back guarantee provided that a patient conforms to a prescription for a specified period of time. In yet another application of some embodiments, a medical service provider such as a doctor, health maintenance organization and/or insurance company may offer preferred rates to their clients who consistently follow prescription instructions. By employing such embodiments, any medical service provider may easily, accurately, and securely verify prescription compliance.

Controller

Figure 9:
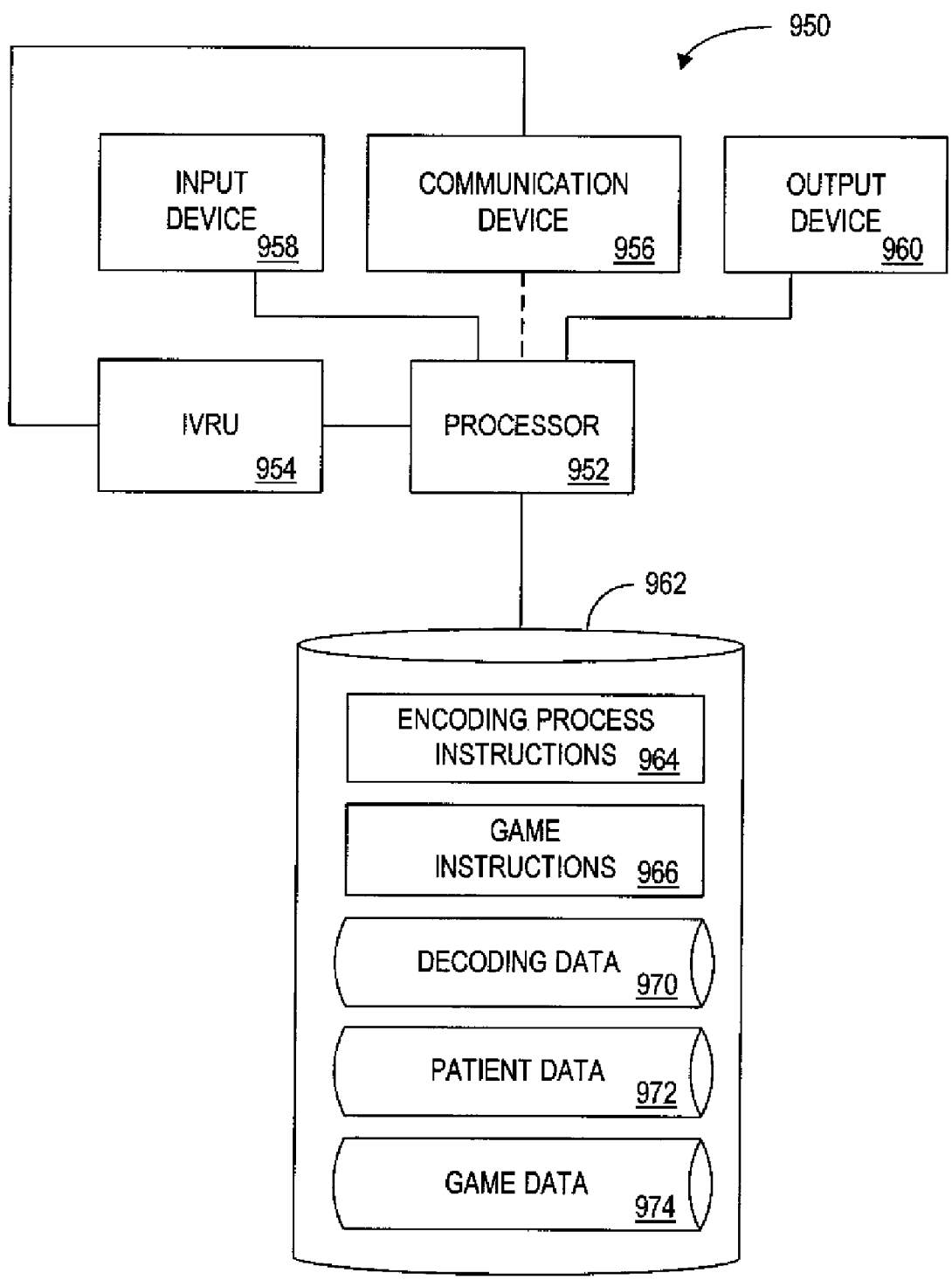
FIG. 9 is a block diagram of a controller according to some embodiments.

Turning to FIG. 9, a block diagram of a controller 950 according to some embodiments is shown. In some embodiments, the controller 950 may be similar in configuration and/or functionality to the controller 150 described in conjunction with FIG. 1. The controller 950 may, for example, be utilized to receive patient compliance and/or game information to provide rewards to patients. The controller 950 may also or alternatively execute, process, and/or otherwise be associated with the method 800 described in conjunction with FIG. 8. In some embodiments, the controller 950 may comprise a processor 952, an IVRU 954, a communication device 956, an input device 958, an output device 960, and/or a data storage device 962. According to some embodiments, the data storage device 962 may store decoding process instructions 964, game instructions 966, decoding data 970, patient data 972, and/or game data 974. In some embodiments, fewer or more components, instructions, and/or data than are shown in FIG. 9 may be included in the controller 950.

According to some embodiments, the processor 952 may be or include any type, quantity, and/or configuration of processor that is or becomes known. The processor 312 may comprise, for example, an Intel® IXP 2800 network processor or an Intel® XEON™ Processor coupled with an Intel® E7501 chipset. In some embodiments, the processor 952 may comprise multiple inter-connected processors, microprocessors, and/or micro-engines. According to some embodiments, the processor 952 (and/or the controller 950 and/or other components thereof) may be supplied power via a power supply (not shown) such as a battery, an Alternating Current (AC) source, a Direct Current (DC) source, an AC/DC adapter, solar cells, and/or an inertial generator. In the case that the controller 950 comprises a server such as a blade server, necessary power may be supplied via a standard AC outlet, power strip, surge protector, and/or Uninterruptible Power Supply (UPS) device.

The IVRU 954 may, according to some embodiments, comprise one or more devices and/or coded instructions (e.g., software or firmware) capable of performing automated and/or substantially automated communications with one or more patients and/or other entities The IVRU 954 may comprise, for example, a software package such as SpeechWorks® Call Navigator™ powered by SpeakFreely® natural language technology, offered by ScanSoft® of Burlington, Mass. According to some embodiments, the processor 952 may receive signals from the IVRU 954, The IVRU 954 may, for example, receive telephone calls and/or input from one or more patients. In some embodiments, the IVRU 954 may receive information indicative of compliance and/or game-related codes supplied to the patients by compliance modules, and/or may provide such information to the processor 952. According to some embodiments, the IVRU 954 may also or alternatively initiate calls and/or other communications with a patient. The IVRU 952 may, for example, initiate a call to a patient to solicit and/or request a compliance and/or game-related code (e.g., provided to the patient by a compliance module).

In some embodiments, the communication device 956 may comprise any type or configuration of communication device that is or becomes known or practicable. The communication device 956 may, for example, comprise a NIC, a telephonic device, a cellular network device, a router, a hub, a modem, and/or a communications port or cable. In some embodiments, the communication device 956 may be coupled to provide communications access to the IVRU 954. The IVRU 954 may, for example, execute telephone and/or other voice or data communications with one or more patients via the communication device 956. According to some embodiments, the communication device 956 may also or alternatively be coupled to the processor 952. The communication device 956 may, for example, comprise a separate device from the IVRU 954. The communication device 956 may, for example, comprise an IR, RF, Bluetooth™, and/or Wi-Fi network device coupled to facilitate communications between the processor 952 and another device (such as a compliance module).

In some embodiments, the input device 958 and/or the output device 960 may comprise any types or configurations of input and output components and/or devices that are or become known, respectively. The input device 960 may comprise, for example, a keyboard that allows an operator of the controller 950 to interface with the controller 950 (e.g., to program, monitor, and/or initiate IVRU 954 sessions). In some embodiments, the input device 958 may comprise a smart card and/or magnetic stripe card reader. The input device 958 may, for example, allow a patient and/or pharmacist to swipe a card associated with a patient (e.g., a smart and/or magnetic stripe insurance card) to provide information such as encoded compliance and/or game-related information to the controller 950 and/or the processor 952. The output device 960 may, according to some embodiments, comprise a display screen and/or other practicable output component and/or device. The output device 960 may, for example, provide feedback to the patient or pharmacist that swipes a smart and/or magnetic stripe card via the input device 958. According to some embodiments, the input device 958 and/or the output device 960 may be similar in configuration and/or functionality to the input device 318 and/or the output device 320 described in conjunction with FIG. 3 herein.

The data storage device 962 may, for example, store the decoding process instructions 964 and/or the game instructions 966 that may be utilized by the processor 952 to provide output information via the output device 958, the IVRU 954, and/or the communication device 956. The data storage device 962 may comprise any appropriate information storage device that is or becomes known or available, including, but not limited to, units and/or combinations of magnetic storage devices (e.g., a hard disk drive), optical storage devices, and/or semiconductor memory devices such as Random Access Memory (RAM) devices, Read Only Memory (ROM) devices, Single Data Rate Random Access Memory (SDR-RAM), Double Data Rate Random Access Memory (DDR-RAM), and/or Programmable Read Only Memory (PROM).

According to some embodiments, the decoding instructions 964 may be operable to cause the processor 952 to decode information. Information received from any of the IVRU 954, the communication device 956, and/or the input device 958 may, for example, be decoded by the processor 952 in accordance with the decoding instructions 964. In some embodiments, encoded compliance and/or game-related information may be received from a patient and/or compliance module, for example, and may be decoded by the processor 952 executing the decoding instructions 964. While any decoding and/or decryption protocol that is or becomes known or practicable may be utilized to decode the information, in some embodiments it may be desirable to employ the same and/or a similar protocol that was utilized to encode the information (e.g., by a compliance module). In some embodiments, the data decoded by the processor 952 (e.g., utilizing the decoding process instructions 964) may comprise prescription compliance information. The number of cap, top, and/or lid removals in a given time period may, for example, be decoded by the processor 952. According to some embodiments, other data may also or alternatively be decoded. Examples of other data may include user identifiers, cap and/or container identifiers, insurance identifiers, account identifiers, compliance module identifiers, a beginning timestamp and an ending timestamp.

In some embodiments, the game instructions 966 may be operable to cause the processor 952 to execute and/or otherwise process data in accordance with one or more games. A patient may interface with the controller 950 (e.g., via the IVRU 954, the communication device 965, and/or the input device 958) to play a game. Access to such a game may be offered, for example, by a compliance module in the case that the patient complies with a prescription-related event and/or achieves some particular compliance goal. In some embodiments, as described elsewhere herein, the compliance module may provide the patient with a telephone number and/or Uniform Resource Locator (URL) or other address via which the patient may access the controller 950 to play the game. The processor 952 may then execute the game instructions 966 to provide and/or render the game for the patient. In some embodiments, the controller 950 may also or alternatively receive game-related information such as an encoded game code from the patient and/or compliance module. The information may be decoded by the processor 952 (e.g., executing the decoding instructions 964), for example, and then utilized to determine on or more game-related events and/or outcomes.

A code received from a patient may trigger a particular game result, for example, and/or may indicate that the patient is eligible for and/or has won a particular prize. According to some embodiments, the patient may play the game via the compliance module and/or another device (e.g., an associated online game) and may provide a "win" code associated with the patient's performance. The processor 952 may then, for example, execute the game instructions 966 to process the code and determine a result associated with the patient's performance achieved in playing the game. According to some embodiments, the game instructions 966 may simply direct the patient and/or the controller 950 to one or more other devices or Web sites associated with playing or downloading games.

The data storage device 962 may also or alternatively store the decoding data 970, the patient data 972, and/or the game data 974. Any or all of these and other types of data may be stored in any number, type, and/or configuration of data storage structures (such as the data storage structures described elsewhere herein) that is or becomes known. The data storage device 962 may, for example, comprise one or more data tables or files, databases, table spaces, registers, and/or other storage structures. In some embodiments, multiple databases and/or storage structures (and/or multiple data storage devices 962) may be utilized to store information associated with the controller 950. According to some embodiments, the data storage device 962 may be incorporated into and/or otherwise coupled to the controller 950 (e.g., as shown) or may simply be accessible to the controller 950 (e.g., externally located and/or situated).

The decoding data 970 may comprise data associated with decoding information via the decoding process instructions 964. The decoding data 970 may comprise, for example, one or more hash values, decryption keys, codes, and/or decoding or decryption algorithms. In some embodiments, the patient data 972 may also or alternatively be stored in the data storage device 962. The patient data 972 may comprise, for example, data associated with patients and/or prescriptions, therapies, and/or other health care regimens associated with patients. According to some embodiments, the patient data 972 may comprise patient contact information, patient account information, medication data, and/or other patient-related information such as a history of prizes or other rewards won or achieved by patients.

The game data 974 may comprise any game-related data that is or becomes known or practicable. The game data 974 may, for example, include data indicative of one or more game boards (e.g., bingo boards, battleship boards, minesweeper boards), card decks (and/or shoes), maps, and/or other game objects. The game data 974 may also or alternatively include one or more moves, actions, values, results, outcomes, pay tables, probability tables, and/or other metrics associated with one or more games. In some embodiments, the game data 974 may comprise one or more files such as picture, sounds, movie, and/or other audio or video files. According to some embodiments, the game data 974 may be utilized by the processor 952 in executing the game instructions 966. The processor 952 may load one or more lottery and/or bingo numbers from the game data 974, for example, to be provided to a complaint patient. These and other aspects of the various types of stored data according to some embodiments are described in more detail with reference to FIG. 10A, FIG. 10B, and FIG. 10C.

Controller Data Tables

Referring now to FIG. 10A, FIG. 10B, and FIG. 10C, block diagrams of data tables 1070, 1072, 1074 according to some embodiments are shown, respectively. In some embodiments, the data tables 1070, 1072, 1074 may be similar in configuration and/or content to the data 970, 972, 974 and/or data tables described in conjunction with FIG. 9. Any or all of the data tables 1070, 1072, 1074 may, for example, be stored in and/or otherwise associated with the controller 150, 950. According to some embodiments, a decoding data table 1070 may store decoding-related information, a patient data table 1072 may store information associated with patients, and/or a game data table 1074 may store game-related information, for example. In some embodiments, fewer or more data fields than are shown may be associated with the data tables 1070, 1072, 1074. Only a portion of one or more databases and/or other data stores is necessarily shown in any of FIG. 10A, FIG. 10B, and/or FIG. 10C, for example, and other database fields, columns, structures, orientations, quantities, and/or configurations may be utilized without deviating from the scope of some embodiments. Similarly, the data shown in the various data fields is provided solely for exemplary and illustrative purposes and does not limit the scope of embodiments described herein.

According to some embodiments, such as shown in FIG. 10A for example, the decoding data table 1070 may comprise various data fields such as a "compliance_module_id" field 1070-1, a "patient_id" field 1070-2, and/or a "key" 1070-3. The "compliance_module_id" field 1070-1 may, for example, simply store an identifier for each compliance module that is issued and/or monitored by and/or otherwise associated with the controller 150, 950. Each compliance module (such as a compliance pad) may, for example, be represented by a unique identifier such as an alphanumeric code stored in the "compliance_module_id" field 1070-1. Each compliance module may also be associated with one or more patients represented by the "patient_id" field 1070-2. In such a manner, for example, compliance modules may be accurately associated with particular patients (and vise versa). The "key" field 1070-3 may contain one or more cryptographic and/or other decoding keys, hash values, metrics, and/or algorithms. Such information may be utilized (e.g., via the decoding process instructions 964) to decode and/or decrypt information received from a compliance module and/or an associated patient. Different cryptographic information (e.g., public and/or private keys) may be stored for different compliance modules and/or patients, or multiple compliance modules and/or patients may be associated with standardized and/or universal cryptographic information.

According to some embodiments, such as shown in FIG. 10B for example, the patient data table 1072 may comprise various data fields such as a "patient_id" field 1072-1, a "phone" field 1072-2, an "insurance_id" field 1072-3, a "condition_id" field 1072-4, a "tamper" field 1072-5, a "score" field 1072-6, and/or a "rank" field 1072-7. The patient data table 1072 may store information associated with various prescriptions, therapies, health care regimens, identification information, and/or other data associated with patients (e.g., patients participating in a wellness program). The "patient_id" field 1072-1 may simply store an identifier (such as a unique identifier) for each registered patient. In some embodiments, the "patient_id" field 1072-1 may link to and/or be otherwise associated with the "patient_id" field 1070-2 of the decoding data table 1070. Contact, identification, and/or demographic information associated with patients may be stored in various data fields as is desirable.

The "phone" field 1072-2 may, for example, store one or more telephone numbers and/or linking identification information (e.g., linking to other tables such as a telephone number table—not shown) associated with a patient. Other information may be similarly stored and/or linked to. Insurance information (such as a health insurance account number) may be represented by and/or linked by the information stored in the "insurance_id" field 1072-3, for example. Conditions associated with a patient's prescriptions may also or alternatively be stored and/or linked to via the patient data table 1072. The "condition_id" field 1072-4 may, for example, link to a table (not shown) containing information describing conditions of a patient's prescriptions. This information may be utilized, for example, to determine if events associated with a patient are in compliance with a prescription. In some embodiments, the "condition_id" field 1072-4 may link to an external table such as via the "condition_id" field 432-1 of the condition data table 432 stored in some compliance modules.

According to some embodiments, the "tamper" field 1072-5 may show whether a compliance module associated with a patient has been tampered with (e.g., "Y" positive tamper indication). In some embodiments, a positive tamper indication associated with a patient via the "tamper" field 1072-5 may disqualify a patient from receiving prizes and/or rewards and/or may cause the patient to be otherwise penalized (e.g., charged a fee for damaging a compliance module).

In some embodiments, the "score" field 1072-6 may contain information (such as the numeric information shown) indicating a score achieved by and/or otherwise associated with a patient. The score may be a score representing compliance, for example, or may represent a patients achievement in a game associated with facilitating compliance. According to some embodiments, the score may indicate a patients score with respect to a competition between patients and/or groups of patients. The "rank" field 1072-7 may, for example, show a ranking (e.g., based on the patients score) of competing patients. All patients in a particular geographical area (e.g., a town, city, state, or zip code), employees of a particular office, members of a particular insurance carrier, and/or members of other pre-defined groups (e.g., Internet groups, clubs, organizations) may, for example, compete for the best compliance (e.g., as represented by the score in the "score" field 1072-6) to win individual and/or group prizes. In some embodiments, the scores and/or rankings may be provided to the patients to further motivate increased compliance (e.g., by stimulating competitive tendencies).

According to some embodiments, such as shown in FIG. 10G for example, the game data table 1074 may comprise various data fields such as a "game_id" field 1074-1, a "game_name" field 1074-2 "win_code" field 1074-3, and/or a "prize" field 1074-4. The game data table 1074 may store information associated with various games used to facilitate and/or enhance patent compliance with prescriptions. The games may be played via a compliance module, a controller, and/or via another device. The "game_id" field 1074-1 may simply store an identifier (such as a unique identifier) for each game, for example, while the "game_name" field 1074-2 may store a name of each game. The games shown in FIG. 10C, for example, are "bingo", "lotto", and "minesweeper". Many other games may also or alternatively be stored and/or used as described elsewhere herein.

In some embodiments, the "win_code" field 1074-3 may store one or more codes and/or other data associated with particular game outputs and/or results. In the case that the game is a form of video poker played via a compliance module and/or via a controller, for example, a code of "ACE93" may be associated with a particular video poker result. In the case that this code is received from a patient (and/or decoded via information received from a patient), for example, a particular card, hand, and/or outcome may be provided to the patient (e.g., via the compliance module and/or controller). In some embodiments, the code may indicate that the patient has "won" the game. A patient having complied with prescription requirements may have been presented with opportunities to play a video poker game via a compliance module, for example, and may have achieved a "winning" result in the game. The compliance module may generate a game code and/or an encoded version thereof and provide the game code to the patient. The patient may then communicate the game code to a controller that may decode the information and compare the resulting game code to the code stored in the game data table 1074. In the case of the video and/or other poker game and received code of "ACE93" shown in FIG. 10C, for example, the matching of the code would indicate that the patient should be awarded one hundred dollars ($100), as stored in the respective "prize" field 1074-4 record.

Rules of Interpretation

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments of the invention nor a listing of features of the invention that must be present in all embodiments.

Neither the Title (set forth at the beginning of the first page of this patent application) nor the Abstract (set forth at the end of this patent application) is to be taken as limiting in any way as the scope of the disclosed invention(s).

The term "product" means any machine, manufacture and/or composition of matter as contemplated by 35 U.S.C. §101, unless expressly specified otherwise.

The terms "an embodiment", "embodiment", "embodiments", "the embodiment", "the embodiments", "one or more embodiments", "some embodiments", "one embodiment" and the like mean "one or more (but not all) disclosed embodiments", unless expressly is specified otherwise.

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present application, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device or article is described herein, more than one device or article (whether or not they cooperate) may alternatively be used in place of the single device or article that is described. Accordingly, the functionality that is described as being possessed by a device may alternatively be possessed by more than one device or article (whether or not they cooperate).

Similarly, where more than one device or article is described herein (whether or not they cooperate), a single device or article may alternatively be used in place of the more than one device or article that is described. For example, a plurality of computer-based devices may be substituted with a single computer-based device. Accordingly, the various functionality that is described as being possessed by more than one device or article may alternatively be possessed by a single device or article.

The functionality and/or the features of a single device that is described may be alternatively embodied by one or more other devices which are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this patent application and the title of this patent application are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining and the like.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software A "processor" means any one or more microprocessors, CPU devices, computing devices, microcontrollers, digital signal processors, or like devices.

The term "computer-readable medium" refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory Volatile media include DRAM, which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during RF and IR data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth™, TDMA, CDMA, 3G.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviors of a database can be used to implement various processes, such as the described herein. In addition, the databases may, in a known manner, be stored locally or remotely from a device that accesses data in such a database.

The present invention can be configured to work in a network environment including a computer that is in communication, via a communications network, with one or more devices. The computer may communicate with the devices directly or indirectly, via a wired or wireless medium such as the Internet, LAN, WAN or Ethernet, Token Ring, or via any appropriate communications means or combination of communications means. Each of the devices may comprise computers, such as those based on the Intel® Pentium® or Centrino™ processor, that are adapted to communicate with the computer. Any number and type of machines may be in communication with the computer.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

What is claimed is:

1. A health care compliance pad, comprising:
   a horizontal surface operable to support a container of a substance;
   a sensor coupled to the horizontal surface, the sensor being operable to detect an occurrence of an event associated with a taking of the substance by a patient;
   a processing device operable to determine, based on a detection, by the sensor, of the occurrence of the event associated with the taking of the substance by the patient, output information associated with a game; and
   an output device operable to provide, to the patient, an indication of the output information associated with the game.

2. The health care compliance pad of claim 1, wherein the health care compliance pad is embodied as one or more of (i) a container stand, (ii) a coaster, (iii) a medicine cabinet, (iv) a shelf, and (v) a shelf or drawer liner.

3. The health care compliance pad of claim 1, wherein the sensor comprises a pressure sensor.

4. The health care compliance pad of claim 3, wherein the pressure sensor is operable to detect the occurrence of the event associated with the taking of the substance by the patient, by being further operable to:
   determine a first pressure associated with the container;
   determine, after the determination of the first pressure, a second pressure associated with the container; and
   determine, by comparing the first and second pressures, whether an amount of the substance is removed from the container.

5. The health care compliance pad of claim 1, wherein the sensor comprises a motion sensor.

6. The health care compliance pad of claim 5, wherein the motion sensor is operable to detect the occurrence of the event associated with the taking of the substance by the patient, by being further operable to:
   determine a removal of the container from the horizontal surface; and
   determine, after the determination of the removal of the container from the horizontal surface, a replacement of the container onto the horizontal surface.

7. The health care compliance pad of claim 6, wherein the sensor further comprises a pressure sensor.

8. The health care compliance pad of claim 7, wherein the pressure sensor is operable to detect the occurrence of the event associated with the taking of the substance by the patient, in conjunction with the motion sensor, by being further operable to:
   determine, prior to the determining of the removal of the container from the horizontal surface, a first pressure associated with the container;
   determine, after the determination of the replacement of the container onto the horizontal surface, a second pressure associated with the container; and
   determine, by comparing the first and second pressures, whether an amount of the substance is removed from the container.

9. The health care compliance pad of claim 1, wherein the sensor comprises a camera.

10. The health care compliance pad of claim 9, wherein the camera is operable to detect the occurrence of the event associated with the taking of the substance by the patient by being further operable to:
    capture one or more images associated with identifying whether a cap of the container is coupled to the container; and
    determining, based at least in part on the one or more captured images, that the cap is (i) removed from the container, or (ii) replaced onto the container.

11. The health care compliance pad of claim 1, wherein the sensor comprises a photocell.

12. The health care compliance pad of claim 11, wherein the photocell is operable to detect the occurrence of the event associated with the taking of the substance by the patient by being further operable to:
    detect a first light level associated with the container;
    detect, after the detection of the first light level, a second light level associated with the container; and
    determine, by comparing the first and second light levels, that a cap associated with the container is (i) removed from the container, or (ii) replaced onto the container.

13. The health care compliance pad of claim 11, wherein the photocell is coupled to detect light levels through a bottom surface of the container.

14. The health care compliance pad of claim 1, wherein the sensor comprises a signal transmitter.

15. The health care compliance pad of claim 14, wherein the signal transmitter is operable to detect the occurrence of the event associated with the taking of the substance by the patient by being further operable to:
    transmit a signal through a bottom surface of the container;
    measure a first characteristic of the transmitted signal;
    measure, after the measuring of the first characteristic, a second characteristic of the transmitted signal; and
    determine, by comparing the first and second characteristics, that a cap associated with the container is (i) removed from the container, or (ii) replaced onto the container.

16. The health care compliance pad of claim 1, wherein the first and second characteristics of the signal comprise one or more of (i) a reflection of the signal, and (ii) a diffraction of the signal.

17. The health care compliance pad of claim 1, wherein the sensor comprises a signal receiver.

18. The health care compliance pad of claim 17, wherein the signal receiver is operable to detect the occurrence of the event associated with the taking of the substance by the patient by being further operable to:
    detect a transmission a signal from a cap of the container.

19. The health care compliance pad of claim 1, wherein the sensor is operable to detect the occurrence of the event associated with the taking of the substance by the patient by being further operable to:
    determine that an electrical circuit comprising a first portion coupled to the horizontal surface and a second portion coupled to a cap of the container, is completed; and
    determine, after the determining that the electrical circuit is completed, that the electrical circuit is not complete.

20. The health care compliance pad of claim 1, wherein the sensor is operable to detect the occurrence of the event associated with the taking of the substance by the patient by being further operable to:
    detect a change in state of an electrical circuit comprising a first portion coupled to the compliance pad and a second portion coupled to the container.

21. The health care compliance pad of claim 1, wherein the output device is further operable to provide the indication of the output information associated with the game by transmitting a signal comprising the indication of the output information associated with the game to a device associated with the patient.

22. The health care compliance pad of claim 21, wherein the device associated with the patient comprises one or more of (i) a computer, (ii) a Personal Digital Assistant (PDA), (iii) a watch, (iv) a TV, (v) a telephone, and (vi) a pager.

23. The health care compliance pad of claim 1, wherein the output information associated with the game comprises one or more of (i) an animated representation of an artificial creature, (ii) a picture of a friend, family member, or celebrity, (iii) a sound recording of a friend, family member, or celebrity, and (iv) an olfactory indicator.

24. The health care compliance pad of claim 1, wherein the processing device is further operable to:
    determine whether the occurrence of the event is compliant with a condition associated with the taking of the substance.

25. The health care compliance pad of claim 24, further comprising:
    a memory device operable to store an indication of the status of the compliance with the condition.

26. The health care compliance pad of claim 25, further comprising:
    an input device operable to receive an indication associated with a query of the status of the compliance with the condition.

27. The health care compliance pad of claim 26, wherein the output device is further operable to provide, in response to a receiving, by the input device, of the indication of the query, an indication of the status of the compliance with the condition.

28. The health care compliance pad of claim 1, wherein the output information comprises one or more of:
    (i) a game result;
    (ii) a game hint or clue;
    (iii) an indication of a prize;
    (iv) an indication of a contingent prize;
    (v) a bingo number;
    (vi) a slot machine reel symbol;
    (vii) a card value;
    (viii) a lotto number;
    (ix) a coordinate associated with game;
    (x) an instruction associated with a game; and
    (xi) a personal identification number.

29. The health care compliance pad of claim 1, wherein the output information is provided as an encoded code.

30. The health care compliance pad of claim 1, wherein the health care compliance pad comprises a flexible medium.

31. A system, comprising:
    a container of a substance;
    a health care compliance pad operable to receive the container of the substance, the health care compliance pad comprising:
        a sensor operable to detect a change in a status of the container of the substance; and
        a processing device operable to determine, based on a detection, by the sensor, of the change in the status of the container of the substance, output information associated with a game; and
        an output device in communication with the processing device, the output device being operable to provide, to the patient, an indication of the output information associated with the game.

32. The system of claim 31, wherein the output device is embodied in the container of the substance.

33. The system of claim 31, wherein the output device is embodied in the health care compliance pad.

34. The system of claim 31, wherein the output device is embodied in a device associated with the patient.

35. The system of claim 34, wherein the device associated with the patient comprises one or more of (i) a computer, (ii) a Personal Digital Assistant (PDA), (iii) a watch, (iv) a TV, (v) a telephone, and (vi) a pager.

36. The system of claim 31, wherein the change in the status of the container of the substance comprises one or more of (i) a movement of the container, (ii) a change in pressure associated with the container, (iii) a removal of a quantity of the substance from the container, (iv) a removal of a cap of the container, and (v) a replacement of the cap of the container.

* * * * *